(12) United States Patent
Vasudevan et al.

(10) Patent No.: US 11,000,516 B2
(45) Date of Patent: May 11, 2021

(54) DOSING REGIMENS OF CELGOSIVIR FOR THE PREVENTION OF DENGUE

(71) Applicants: 60 Degrees Pharmaceuticals, LLC, Washington, DC (US); National University of Singapore, Singapore (SG); Singapore Health Services PTE Ltd., Singapore (SG)

(72) Inventors: Subhash Vasudevan, Singapore (SG); Geoffrey S. Dow, Washington, DC (US); Satoru Watanabe, Singapore (SG); Eng Eong Ooi, Singapore (SG); Jenny Low, Singapore (SG); Kitti Wing Ki Chan, Singapore (SG)

(73) Assignees: 60 Degrees Pharmaceuticals, LLC, Washington, DC (US); National University of Singapore, Singapore (SG); Singapore Health Services PTE Ltd., Singapore (SG)

( * ) Notice: Subject to any disclaimer, the term of this patent is extended or adjusted under 35 U.S.C. 154(b) by 0 days.

(21) Appl. No.: 16/060,945

(22) PCT Filed: Dec. 9, 2016

(86) PCT No.: PCT/US2016/065719
§ 371 (c)(1),
(2) Date: Jun. 10, 2018

(87) PCT Pub. No.: WO2017/100505
PCT Pub. Date: Jun. 15, 2017

(65) Prior Publication Data
US 2018/0360809 A1     Dec. 20, 2018

Related U.S. Application Data

(60) Provisional application No. 62/266,119, filed on Dec. 11, 2015.

(51) Int. Cl.
*A61K 31/437* (2006.01)
*A61P 31/14* (2006.01)
*A61K 9/00* (2006.01)

(52) U.S. Cl.
CPC .......... *A61K 31/437* (2013.01); *A61K 9/0019* (2013.01); *A61P 31/14* (2018.01); *Y02A 50/30* (2018.01)

(58) Field of Classification Search
CPC .............................. A61K 31/437; A61P 31/14
See application file for complete search history.

(56) References Cited

U.S. PATENT DOCUMENTS 10,517,854 B2 * 12/2019 Dow ................. A61P 31/14
2004/0147549 A1 * 7/2004 Tyms ................. A61K 31/00
514/306

FOREIGN PATENT DOCUMENTS

WO   WO 2014/143907      9/2014
WO   WO-2014143907 A1 *  9/2014  ........... A61K 31/437

* cited by examiner

*Primary Examiner* — Theodore R. Howell
(74) *Attorney, Agent, or Firm* — Panitch Schwarze Belisario & Nadel LLP

(57) ABSTRACT

Methods of preventing a disease resulting from a dengue virus (DENV) infection in a human subject, comprising administering to the human subject a compound of Formula (I), or pharmaceutical composition comprising a compound of Formula (I); a compound of Formula (I) can be first administered to an asymptomatic human subject followed by subsequent doses administered at least once daily. The methods of the invention can be used to prevent a disease resulting from primary and secondary DENV 1-4 viral infections.

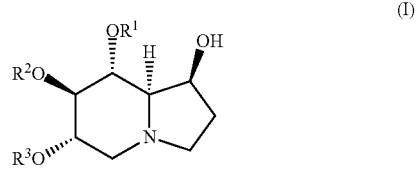

24 Claims, 8 Drawing Sheets

013

031

036

DOSING REGIMENS OF CELGOSIVIR FOR THE PREVENTION OF DENGUE

CROSS-REFERENCE TO RELATED APPLICATIONS

This application is a U.S. National Stage Application pursuant to 35 U.S.C. § 371 of International Patent Application PCT/US2016/065719, filed on Dec. 9, 2016, and published as WO 2017/100505 on Jun. 15, 2017, which claims priority to U.S. Provisional Patent Application 62/266,119, filed on Dec. 11, 2015, all of which are incorporated herein by reference in their entireties for all purposes.

BACKGROUND OF THE INVENTION

Globally, dengue infections result in more than 20,000 deaths, nearly 500,000 hospitalized cases and anywhere between 50-100 million human infections annually. (1) Dengue infection is caused by one of four immunologically distinct serotypes of the dengue virus (DENV 1-4). The virus is spread by the urban breeding mosquito *Aedes aegypti*. Usually, infection with any one of the four DENV serotypes leads to mild, self-limiting dengue fever with lifelong immunity to the specific serotype of infection. Epidemiological evidence also indicates that 90% of the severe and potentially fatal dengue diseases, dengue hemorrhagic fever (DHF) or dengue shock syndrome (DSS) occur during secondary heterotypic infections where the protective antibody from a prior infection takes on a pathogenic role, so-called Antibody Dependent Enhancement (ADE). (2, 3) The antibody response triggers a systemic inflammatory reaction resulting in vascular leakage.

Currently, there is no approved preventive vaccine or antiviral prophylactic for dengue disease. The World Health Organization has listed dengue fever as an emerging and uncontrolled disease. (4) Hence, there is an urgent medical need for the development of a potent dengue antiviral that is safe for use in humans.

SUMMARY OF THE INVENTION

The present invention pertains to methods of preventing a disease resulting from a dengue virus (DENV) infection in a human subject. In one aspect, the method comprises administering to the human subject at least one initial (loading) dose of about 40 to 600 mg of a compound of Formula (I) or a pharmaceutically acceptable salt thereof, or a pharmaceutical composition comprising about 40 to 600 mg of a compound of Formula (I) or a pharmaceutically acceptable salt thereof, followed by administration of a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein the human subject is asymptomatic at the time of administration of the at least one initial dose.

In one embodiment, the subsequent doses are administered at intervals of from about 6 to about 12 hours. In other embodiments, the subsequent doses are administered about every 6 hours, about every 8 hours, about every 12 hours, or about every 24 hours. In further embodiments, the subsequent doses are administered at least once, twice, three, four, or five times per day. In still further embodiments, the subsequent doses are administered one or more, two or more, three or more, four or more, or five or more times per day. In certain embodiments, when multiple subsequent doses are given daily, they are approximately evenly spaced throughout a 24 hour period.

In certain embodiments, the total amount of a compound of Formula (I) does not exceed 600 mg per day. In other embodiments the total amount of a single administration of a compound of Formula (I) is 400 mg or less.

In certain embodiments, the subsequent doses are administered during potential exposure of at least one serotype of dengue virus. In other embodiments, the subsequent doses are administered for about 1-10 days, about 1-15 days, about 1-20 days, about 1-25 days, about 30 days, about four weeks, about six weeks, about eight weeks, about three months, about four months, about five months, about six months, about seven months, about eight months, about nine months, about ten months, about eleven months, or about one year. In other embodiments, the subsequent doses are administered for about 5-20 days, 5-30 days, 10-40 days, or 10-50 days.

In the various embodiments, the human subject can be an adult or a child.

The compound of Formula (I) is represented by the following structure:

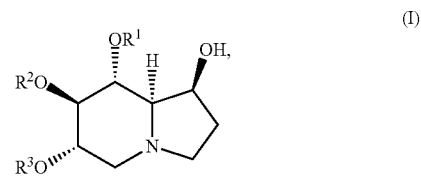

or a pharmaceutically acceptable salt thereof;
wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

In certain embodiments, the compound of Formula (I) is specifically the compound of Formula (II), below, or a pharmaceutically acceptable salt thereof:

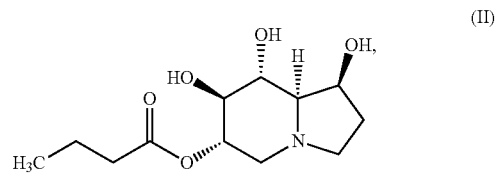 [SMILES: CCCC(=O)O[C@H]1CN2CC[C@H](O)[C@@H]2[C@@H](O)[C@@H]1O]

In preferred embodiments, the compound of Formula (I) is a prodrug of castanospermine, a natural product derived from the seeds of *Castanospermum australe*. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher 50% effective concentration (EC50) values and in vivo efficacy than castanospermine against the dengue (DENV) virus.

In certain embodiments, the at least one initial dose comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 27, at least 28, at least 29, or at least 30 doses. In other embodiments, the at least one initial dose comprising one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, at most 24, at most 25, at most 27, at most 28, at most 29, or at most 30 doses. In some embodiments, two or more initial doses are administered at intervals of from about 6 to about 12 hours. In other embodiments, two or more initial doses are administered about every 6 hours, about every 8 hours, about every 12 hours, or about every 24 hours. In further embodiments, two or more initial doses are administered once, twice, three, four, or five times per day. In still further embodiments, the initial doses are administered one or more, two or more, three or more, four or more, or five or more times per day. In certain embodiments, when multiple initial doses are given daily, they are approximately evenly spaced throughout a 24 hour period.

In certain embodiments, the beginning of the administration of the subsequent doses is within a day of administration of the at least one initial dose. In further embodiments, the beginning of the administration of the subsequent doses is about 20 hours, about 15 hours, about 12 hours, about 8 hours, or about 6 hours after administration of the at last one initial dose.

In certain embodiments, at least one initial dose is the same as the subsequent doses, while in other embodiments the at least one initial dose differs from the subsequent doses. In particular embodiments, the at least one initial dose is higher than the subsequent doses. In further embodiments, the at least one initial dose is the same dosage amount throughout the method. In other embodiments, the at least one initial dose varies dosage amounts throughout the method. In further embodiments, the plurality of subsequent doses is the same dosage amount throughout the method. In other embodiments, the plurality of subsequent doses varies dosage amounts throughout the method.

In certain embodiments, for an adult subject, the initial dose of a compound of Formula (I) can be between about 40 to about 600 mg. In other embodiments, the initial dose of a compound of Formula (I) in an adult subject can be about 75-600 mg, 100-600 mg, 150-600 mg, about 200-500 mg, or about 250-400 mg. In further embodiments, the initial dose of a compound of Formula (I) in an adult subject can be about 40 mg, about 60 mg, about 80 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose of a compound of Formula (I) in an adult subject is between about 550 to about 600 mg. In another embodiment, the initial dose of a compound of Formula (1) in an adult subject is between about 500 to about 550 mg. In yet another embodiment, the initial dose of a compound of Formula (I) in an adult subject is between about 450 to about 500 mg. In a further embodiment, the initial dose of a compound of Formula (I) in an adult subject is between about 400 to about 450 mg. In another embodiment, the initial dose of a compound of Formula (I) in an adult subject is between about 350 to about 400 mg. In further embodiment, the initial dose of compound of Formula (I) in an adult subject is between about 300 to about 350 mg. In yet another embodiment, the initial dose of a compound of Formula (I) in an adult subject is between about 250 to about 300 mg. In further embodiment, the initial dose of compound of Formula (I) in an adult subject is between about 200 to about 250 mg. In another embodiment, the initial dose of a compound of Formula (I) in an adult subject is between about 150 to about 200 mg. In another embodiment, the initial dose of compound of Formula (I) in an adult subject is between about 100 to about 150 mg. In further embodiments, the initial dose of a compound of Formula (I) in an adult subject is between about 50 to about 100 mg.

The subsequent doses of a compound of Formula (I) in an adult subject can be between about 40 to about 400 mg. In one embodiment, the subsequent dose of a compound of Formula (I) in an adult subject is between about 250 to about 300 mg. In another embodiment the subsequent dose of a compound of Formula (I) in an adult subject is between about 200 to about 250 mg. In yet another embodiment, the subsequent dose of a compound of Formula (I) in an adult subject is between about 150 to about 200 mg. In a further embodiment, the subsequent dose of a compound of Formula (I) in an adult subject is between about 100 to about 200 mg. In other embodiments, the subsequent dose of a compound of Formula (I) in an adult subject is between about 40 to about 80 mg. In even further embodiments, the subsequent dose of a compound of Formula (I) in an adult subject is between about 80 to about 100 mg. In an additional embodiment, the subsequent dose of a compound of Formula (I) in an adult subject is between about 125 to about 175 mg. In yet another embodiment, the subsequent dose of a compound of Formula (I) in an adult subject is about 150 mg.

For a child subject, the initial dose of a compound of Formula (I) in a child subject can be between about 25 to about 450 mg. In one embodiment, the initial dose of a compound of Formula (I) in a child subject is between about 25 to about 50 mg. In another embodiment, the initial dose of a compound of Formula (I) in a child subject is between about 50 to about 75 mg. In yet another embodiment, the initial dose of a compound of Formula (I) in a child subject is between about 75 to about 100 mg. In further embodiment, the initial dose of a compound of Formula (I) in a child subject is between about 100 to about 150 mg. In another embodiment, the initial dose of a compound of Formula (I) in a child subject is between about 150 to about 200 mg. In yet another embodiment, the initial dose of a compound of Formula (I) in a child subject is between about 200 to about 250 mg. In a further embodiment, the initial dose of a compound of Formula (I) in a child subject is between about 250 to about 300 mg. In another embodiment, the initial dose of a compound of Formula (I) in a child subject is between about 300 to about 350 mg. In yet another embodiment, the initial dose of a compound of Formula (I) in a child subject is between about 350 to about 400 mg.

The subsequent doses of a compound of Formula (I) in a child subject can be between about 25 to about 200 mg. In one embodiment, the subsequent dose of a compound of Formula (I) in a child subject is between about 25 to about 50 mg. In another embodiment, the subsequent dose of a compound of Formula (I) in a child subject is between about 50 to about 75 mg. In yet another embodiment, the subsequent dose of a compound of Formula (I) in a child subject is between about 75 to about 100 mg. In further embodiment, the subsequent dose of a compound of Formula (I) in a child subject is between about 100 to about 125 mg. In another embodiment, the subsequent dose of a compound of Formula (I) in a child subject is between about 125 to about 150 mg. In yet another embodiment, the subsequent dose of a compound of Formula (I) in a child subject is between about 150 to about 200 mg.

In one embodiment, the initial dose(s) is administered to an asymptomatic human subject. The compounds or pharmaceutical compositions of the present invention can be administered intravenously, orally, rectally or sublingually. In one embodiment, the route of administration is intravenous. In another embodiment, the route of administration is oral. In another embodiment, the route of administration is rectal. In yet another embodiment, the route of administration is sublingual.

The compounds or pharmaceutical compositions of the present invention can be administered as a single or as a divided dose. In some embodiments, the at least one initial dose can be single, divided, or a combination thereof. In some embodiments, the subsequent doses can be single, divided, or a combination thereof. For the subsequent doses in one embodiment, the human subject is administered a divided dose of from about 25 to about 400 mg of a compound of Formula (I), or a pharmaceutical composition comprising a compound of Formula (I), for between about 5 to about 30 days. In another embodiment, the human subject is administered the subsequent doses as a single dose of from about 25 to about 400 mg of a compound of Formula (I), or a pharmaceutical composition comprising a compound of Formula (I), for between about 5 to about 40 days. In yet another embodiment, the human subject is administered the subsequent doses as a single dose of from about 25 to about 400 mg of a compound of Formula (I), or a pharmaceutical composition comprising a compound of Formula (I), for between about 5 day to about 60 days. In a further embodiment, the human subject is administered the subsequent doses as a single dose of from about 25 to about 400 mg of a compound of Formula (I), or a pharmaceutical composition comprising a compound of Formula (I), for between about 5 days to about 60 days. In other versions, the subsequent doses are administered no longer than about 10 days; in yet other versions no longer than about 20 days; in further versions no longer than about 50 days; other versions no longer than about 100 days; and in other versions no longer than about one year.

The invention also relates to methods of preventing a disease resulting from a dengue virus infection by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In another aspect, the invention relates to methods for preventing a disease resulting from a dengue viral infection comprising at least one dengue virus selected from DENV1, DENV2, DENV3, and DENV4. In one embodiment, the dengue virus is DENV1. In another embodiment, the dengue virus is DENV2. In yet another embodiment, the dengue virus is DENV3. In further embodiment, the dengue virus is DENV4.

In yet another aspect, the invention relates to methods of preventing a disease resulting from a dengue viral infection in a human subject who has tested negative for dengue virus. Known methods for diagnosis of dengue viral infection can be used including, but not limited to, an NS1 (nonstructural protein 1) strip assay or a quantitative Polymerase Chain Reaction (PCR) assay.

The invention also relates to methods of preventing a disease resulting from a secondary dengue (DENV) viral infection in a human subject, comprising administering to the human subject at least one initial dose of about 40 to about 600 mg of a compound of Formula (I) or a pharmaceutically acceptable salt thereof, or a pharmaceutical composition comprising about 40 to about 600 mg a compound of Formula (I) or a pharmaceutically acceptable salt thereof, and administering to the human subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, and wherein said subsequent doses are administered once, twice, three, or four times per day during potential exposure of at least one serotype of dengue virus.

In another aspect of the invention, viral load reduction of human subjects receiving the method of prevention is at least 50% greater than in persons not administered the compound or in placebo-administered groups. In one embodiment, the virological log reduction in human subjects receiving the method of prevention with a compound of Formula (I) is at least 50% greater than in persons not administered the compound or in placebo-administered groups. In another embodiment, the virological log reduction in human subjects receiving the method of prevention with a compound of Formula (I) is between about 60% to about 70% greater than in persons not administered the compound or in placebo-administered groups. In another embodiment, the virological log reduction in human subjects receiving the method of prevention with a compound of Formula (I) is between about 70% to about 80% greater than in persons not administered the compound or in placebo-administered groups. In yet another embodiment, the virological log reduction in human subjects receiving the method of prevention with a compound of Formula (I) is between about 80 to about 90% greater than in persons not administered the compound or in placebo-administered groups.

The invention is also directed to methods of preventing a disease resulting from a dengue viral infection comprising administering a pharmaceutical composition comprising a compound of Formula (I), Formula (II), or Formula (III) according to any one of the dosing regimens described herein. The disclosed compounds of Formula (I), Formula (II) or Formula (II) can be administered to the subject in conjunction with an acceptable pharmaceutical carrier or diluent as part of a pharmaceutical composition for prevention of a disease resulting from a dengue (DENV) infection.

BRIEF DESCRIPTION OF THE DRAWINGS

The foregoing will be apparent from the following more particular description of example embodiments of the invention, as illustrated in the accompanying drawings.

FIG. 5B shows celgosivir improves survival of DENV2 infected mice in a lethal ADE model of viremia in a dose- and schedule-dependent manner. Survival at day 12 was 1/8 (13%) at 10 mg/kg twice daily (BID), 5/8 (63%) at 25 mg/kg BID, 7/7 (100%) at 50 mg/kg BID, and 0/8 (0%) at 100 mg/kg once daily (QD).

DETAILED DESCRIPTION OF THE INVENTION

Figure 1:
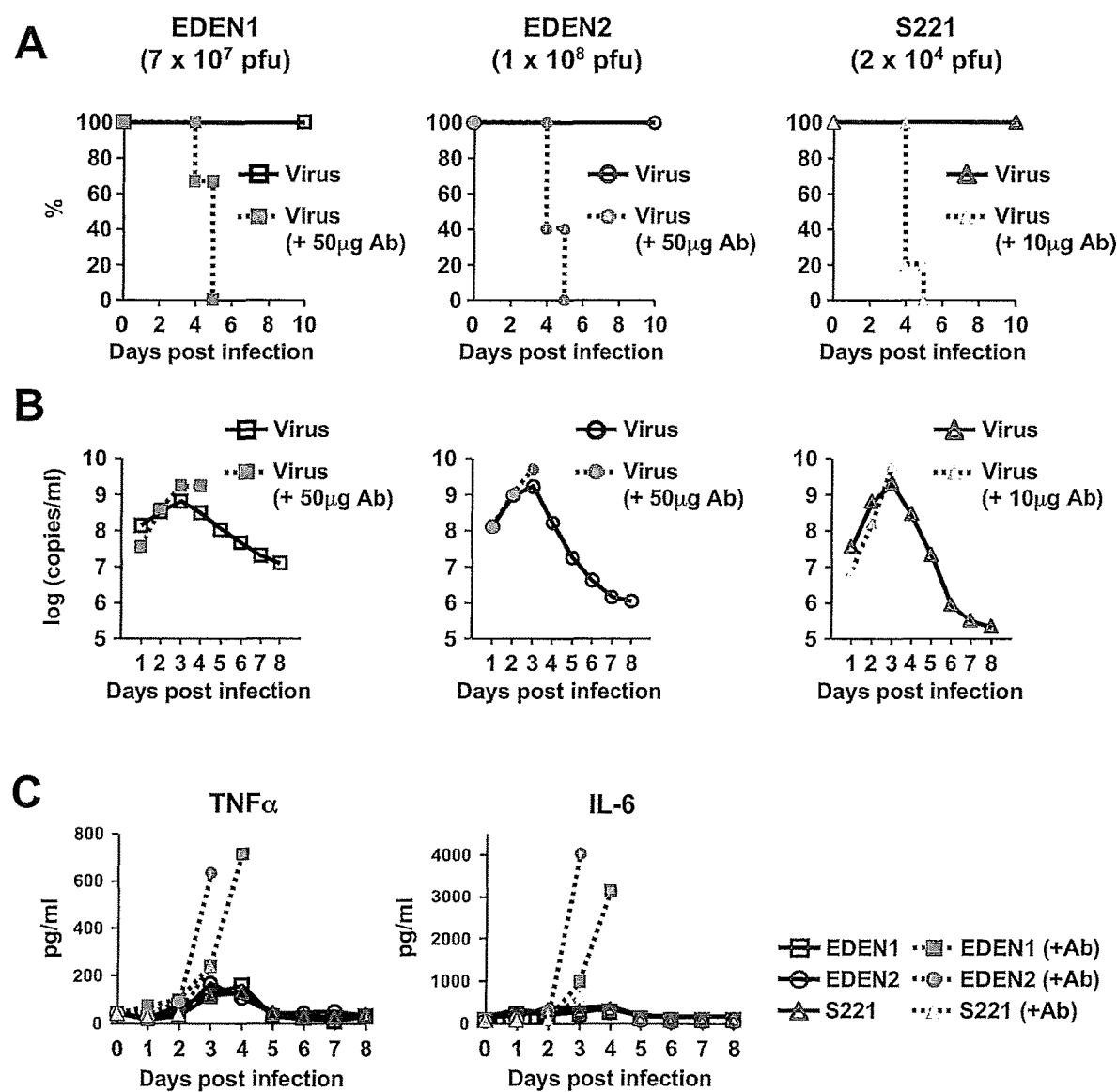
FIG. 1 shows infections models of EDEN1, EDEN2 and S221 in AG129 mice. AG129 mice were inoculated i.v. with EDEN1 ($7 \times 10^7$ pfu), EDEN2 ($1 \times 10^8$ pfu) or S221 ($2 \times 10^4$ pfu) for non-lethal infection. For the ADE infection (lethal), mice were pre-injected i.p. with 50 μg (for EDEN1 and EDEN2) or 10 μg (for S221) 4G2 Ab one day prior to infection. (A) Mouse survival rate was monitored by day 10 pi. (B) Blood samples were collected on days 1-8 pi and mixed serum from each group were subjected to real-time RT-PCR to obtain the average viral genome copy numbers. (C) Serum levels of TNFα and IL-6 were measured by ELISA assay. The numbers of mice per group are 6 (EDEN1) or 5 (EDEN2 and S221).

A description of example embodiments of the invention follows.

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

"Alkyl" as used alone or as part of a larger moiety as in "arylalkyl" or "aryloxyalkyl" means a saturated aliphatic branched or straight-chain monovalent hydrocarbon radicals, typically $C_1$-$C_{16}$, preferably $C_1$-$C_{12}$. For example, "($C_1$-$C_6$) alkyl" means a radical having from 1-6 carbon atoms in a linear or branched arrangement. "($C_1$-$C_6$) alkyl" includes methyl, ethyl, propyl, butyl, tert-butyl, pentyl and hexyl.

"Alkylene" means a saturated aliphatic straight-chain divalent hydrocarbon radical. Thus, "($C_1$-$C_6$) alkylene" means a divalent saturated aliphatic radical having from 1-6 carbon atoms in a linear arrangement. "($C_1$-$C_6$) alkylene" includes methylene, ethylene, propylene, butylene, pentylene and hexylene.

"Cycloalkyl" means saturated aliphatic cyclic hydrocarbon ring. Thus, "$C_3$-$C_8$ cycloalkyl" means (3-8 membered) saturated aliphatic cyclic hydrocarbon ring. $C_3$-$C_8$ cycloalkyl includes, but is not limited to cyclopropyl, cyclobutyl, cyclopentyl, cyclohexyl, cycloheptyl, and cyclooctyl. Preferably, cycloalkyl is $C_3$-$C_6$ cycloalkyl.

The term "alkoxy" means —O-alkyl; "arylalkoxy" means an alkoxy group substituted at any carbon by an aryl group; "hydroxyalkyl" means alkyl substituted with hydroxy; "arylalkyl" means alkyl substituted with an aryl group; "alkoxyalkyl" mean alkyl substituted with an alkoxy group; "cycloalkylalkyl" means alkyl substituted with cycloalkyl; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$) alkyl and includes methoxy, ethoxy, propoxy, butoxy, pentoxy and hexoxy.

"Cycloalkoxy" means a cycloalkyl-O— group wherein the cycloalkyl is as defined above. Exemplary ($C_3$-$C_7$) cycloalkyloxy groups include cyclopropoxy, cyclobutoxy, cyclopentoxy, cyclohexoxy and cycloheptoxy.

"Halogen" and "halo" are interchangeably used herein and each refers to fluorine, chlorine, bromine, or iodine.

The terms "haloalkyl", "halocycloalkyl" and "haloalkoxy" mean alkyl, cycloalkyl, or alkoxy, as the case may be, substituted with one or more halogen atoms. The term "halogen" or "halo" means F, Cl, Br or I.

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

An "alkylene group" is represented by —[$CH_2$]$_z$—, wherein z is a positive integer, preferably from one to eight, more preferably from one to four.

An "alkenylene group" is an alkylene in which at least a pair of adjacent methylenes are replaced with —CH=CH—.

The term "($C_6$-$C_{10}$) aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-10 ring atoms. A "substituted aryl group" is substituted at any one or more substitutable ring atom. The term "$C_6$-$C_{16}$ aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like. The ($C_6$-$C_{10}$) aryl ($C_1$-$C_6$) alkyl group connects to the rest of the molecule through the ($C_1$-$C_6$) alkyl portion of the ($C_6$-$C_{10}$) aryl ($C_1$-$C_6$) alkyl group.

The term "Alkenyl" as used alone or as part of a larger moiety as in "Alkenylacyl" or "haloalkylacyl" means a straight or branched hydrocarbon radical having a specified number of carbon atoms and includes at least one double bond. An alkenyl group generally has between 2 and 6 carbon atoms. The ($C_6$-$C_{10}$) aryl ($C_2$-$C_6$) alkenyl group connects to the remainder of the molecule through the ($C_2$-$C_6$) alkenyl portion of ($C_6$-$C_{10}$) aryl ($C_2$-$C_6$) alkenyl.

"Alkenylacyl" refers to an acyl group, R"—C(O)—, where R" is an alkenyl or a substituted alkenyl (e.g., $CH_3$—CH=CH—C(O)—).

"Pharmaceutically acceptable carrier" means non-therapeutic components that are of sufficient purity and quality for use in the formulation of a composition of the invention that, when appropriately administered to typically do not produce an adverse reaction, and that are used as a vehicle for a drug substance (e.g., a compound of Formula (I)).

"Intraperitoneal injection," as used herein, refers to the injection of a substance into the peritoneum (body cavity).

"Three times a day dosing" or "three times per day," as used herein, refers to three administrations of a composition per every 24 hour period.

"Four times a day dosing" (QDS) or "four times per day," as used herein, refers to four administrations of a composition per every 24 hour period.

As used herein, "BDI" refers to twice daily. Further, as used herein, "QD" refers to once daily.

As used herein, "Cmin" refers to the minimum concentration that a drug achieves after the drug has been administered and prior to the administration of a second or additional dose. Further, "Cmax", as used herein, refers to the maximum concentration. Similarly, "Tmax", as used herein, refers to the time of maximum concentration. Additionally, "AUC", used herein, is the area under the concentration-time curve. Additionally, "50% effective concentration" (EC50), as used herein, refers to the concentration of an anti-viral that produces 50% of the maximal possible antiviral effect.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

The abbreviation "DENV", as used herein, refers to dengue virus. Further the four serotypes of the dengue virus are used herein as "DENV1", "DENV2", "DENV3", and "DENV4".

"Antibody enhanced" or "Antibody Dependent Enhancement" (ADE), as used herein interchangeably, refers to a DENV infection made more severe due to a prior infection with one of the four DENV serotypes: DENV1, DENV2, DENV3, and DENV4.

As used herein, "dengue hemorrhagic fever" (DHF) and "dengue shock syndrome" (DSS), refers to the severe and potentially fatal dengue diseases that often occur during secondary heterotypic infections.

As used herein, "viral load" refers to the amount of virus in the blood stream of a human subject.

As used herein, "initial dose" refers to the dose(s) which is administered to an asymptomatic human subject. Further, "loading dose" and "initial dose" have the same meaning and are used interchangeably herein.

As used herein, "potential exposure," "deployment," and "travel" refers to the period of time between entry and exit of a human subject into/from a geographical area where they may be exposed to *Aedes aegypti* mosquitoes harboring one or more stereotypes of dengue virus.

As used herein, "asymptomatic" refers to a human subject that may have been exposed to *Aedes aegypti* mosquitoes harboring one or more stereotypes of dengue virus but does not present symptoms related to a dengue virus infection, such as fever or diarrhea, or refers to a human subject that has not been exposed to *Aedes aegypti* mosquitoes harboring one or more stereotypes of dengue virus (e.g., the human subject is not located in or has not recently traveled to a geographical area where *Aedes aegypti* mosquitoes harboring one or more stereotypes of dengue virus are indigenous).

Dosing Regimen

The present invention pertains to methods of preventing a disease resulting from a dengue virus (DENV) infection in a human subject, comprising administering to the human subject an initial dose of about 40 to about 600 mg of a compound of Formula (I) or a pharmaceutically acceptable salt thereof, or a pharmaceutical composition comprising about 40 to about 600 mg of a compound of Formula (I) or a pharmaceutically acceptable salt thereof, and administering to the human subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, and wherein said subsequent doses are administered once, twice, three, or four times per day during potential exposure of at least one serotype of dengue virus. In further embodiments, the subsequent doses are administered one or more, two or more, three or more, four or more, or five or more times per day. In certain embodi- ments, when multiple subsequent doses are given daily, they are approximately evenly spaced throughout a 24 hour period.

In one embodiment, the compound of the invention is a compound of Formula (I):

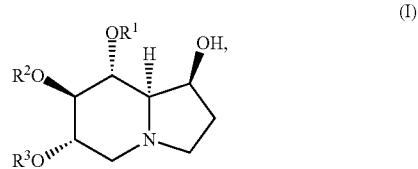

or a pharmaceutically acceptable salt there of;
wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

In another embodiment, $R^1$ and $R^2$ are H and $R^3$ is a $(C_1-C_{14})$ acyl. In another embodiment, $R^1$ is $CH_3$—$CH_2CH_2$—$C(O)$—. In yet another embodiment, $R^2$ is $CH_3$—$CH_2CH_2$—$C(O)$—. In a further embodiment, $R^3$ is $CH_3$—$CH_2CH_2$—$C(O)$—. In another embodiment, at least one but not more than two $R^1$, $R^2$, and $R^3$ is a hydrogen.

In yet another embodiment, the compound of the invention is a compound of Formula (II):

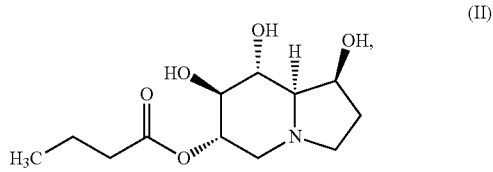 [SMILES: CCCC(=O)O[C@H]1CN2CC[C@H](O)[C@@H]2[C@@H](O)[C@@H]1O]

or a pharmaceutically acceptable salt thereof.

The compound of Formula (II), or pharmaceutical composition comprising a compound of Formula (II), can be used in any of the embodiments provided herein for Formula (I).

In further embodiment, the compound of the invention is a compound of Formula (III):

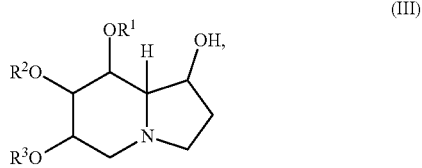

or a pharmaceutically acceptable salt there of;
wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

The compound of Formula (III), or pharmaceutical composition comprising a compound of Formula (III), can be used in any of the embodiments provided herein for Formula (I).

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt. In another embodiment, the compound of Formula (II) is a hydrochloride salt.

The invention is also directed to methods of the invention using a pharmaceutical composition comprising a compound of Formula (I) or Formula (II). The disclosed compounds of Formula (I) and Formula (II) can be administered to the subject in conjunction with an acceptable pharmaceutical carrier or diluent as part of a pharmaceutical composition for prevention of a disease resulting from a dengue (DENV) infection, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the pharmaceutical composition comprises a pharmaceutically acceptable carrier or diluent and a compound Formula (I). In another embodiment, the pharmaceutical composition comprises a pharmaceutically acceptable carrier or diluent and a compound Formula (II).

In preferred embodiments, the compound of Formula (I) is prodrug of castanospermine, a natural product derived from the seeds of *Castanospermum australe*. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher $EC_{50}$ values and in vivo efficacy than castanospermine against the dengue (DENV) virus.

Castanospermine has been shown to exert antiviral activity by inhibiting host alpha-glucosidases I and II, enzymes essential for proper folding of dengue-virus encoded glycoproteins such as E and prM. (6, 7) Castanospermine targets dengue NS1 protein folding in dengue virus infected cells. Impaired glycosylation of the NS1 protein leads to accumulation of proteins in the endoplasmic reticulum (ER) and drastically inhibits the virus replication. Since the drug target is a host enzyme required for viral maturation, the potential for development of resistance is expected to be lower than a drug directed against a viral enzyme.

The methods of the invention prevent a human subject from having a disease resulting from a dengue viral infection. As used herein "preventing" or "prevention" refers to obtaining desired pharmacological and/or physiological effects. The effect can include achieving, partially or substantially one or more of the following results: partially or totally avoiding the disease, disorder or syndrome resulting from a dengue viral infection; or partially or totally avoiding clinical symptom or indicator associated with the disease, disorder, or syndrome resulting from a dengue viral infection; or reducing the severity of the disease, disorder, or syndrome resulting from a dengue viral infection.

The initial dose of a compound of Formula (I) or a pharmaceutically acceptable salt thereof, or a pharmaceutical composition comprising a compound of Formula (I) or a pharmaceutically acceptable salt thereof, can be administered at any time in an asymptomatic human subject. In one embodiment, the initial dose is administered at the time of exposure to at least one serotype of dengue virus. In another embodiment, the initial dose is administered prior to fever onset. Subsequent doses can be the same amount or vary to achieve steady state Cmin or plasma concentrations in the subject.

The human subject may be an adult or a child. As used herein, a "child" refers to a human subject who is between the ages of 1 day to 17 years of age. The term "adult" refers to a human subject who is 18 years of age or older. Further, the plurality of human subjects may include adults or children. In some embodiments, the plurality of human subjects may include only adults. In another embodiment, the plurality of human subjects may include only children. In yet another embodiment, the plurality of human subjects may include both adults and children.

In another aspect, the present invention relates to a method of preventing a disease resulting from a dengue invention in an adult subject comprising administering to the adult subject at least one initial dose of about 40 to about 600 mg of a compound of Formula (I) or a pharmaceutically acceptable salt thereof, or a pharmaceutical composition comprising about 40 to about 600 mg of a compound of Formula (I) or a pharmaceutically acceptable salt thereof, and administering to the adult subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof. In further embodiments, not more than 600 mg is administered per day. In yet other embodiments, the human subject is asymptomatic at the time of administration of the at least one initial dose. In another embodiment, the subsequent doses are administered once, twice, three, or four times per day during potential exposure of at least one serotype of dengue virus.

Example embodiments of initial and subsequent doses in an adult are shown in Table 1:

TABLE 1

Dosing Regimen for an Adult

| Embodiment | Initial dose (mg)[1] | Subsequent dose (mg)[2] |
|---|---|---|
| 1 | 100 | 100 |
| 2 | 150 | 100 |
| 3 | 200 | 100 |
| 4 | 250 | 100 |
| 5 | 300 | 100 |
| 6 | 350 | 100 |
| 7 | 400 | 100 |
| 8 | 450 | 100 |
| 9 | 500 | 100 |
| 10 | 550 | 100 |
| 11 | 600 | 100 |
| 12 | 100 | 150 |
| 13 | 150 | 150 |
| 14 | 200 | 150 |
| 15 | 250 | 150 |
| 16 | 300 | 150 |
| 17 | 350 | 150 |
| 18 | 400 | 150 |
| 19 | 450 | 150 |
| 20 | 500 | 150 |
| 21 | 550 | 150 |
| 22 | 600 | 150 |
| 23 | 600 | 175 |
| 24 | 100 | 200 |
| 25 | 150 | 200 |
| 26 | 200 | 200 |
| 27 | 250 | 200 |
| 28 | 300 | 200 |
| 29 | 350 | 200 |
| 30 | 400 | 200 |
| 31 | 450 | 200 |
| 32 | 500 | 200 |
| 33 | 550 | 200 |
| 34 | 600 | 200 |
| 35 | 100 | 250 |
| 36 | 150 | 250 |
| 37 | 200 | 250 |
| 38 | 250 | 250 |
| 39 | 300 | 250 |
| 40 | 350 | 250 |
| 41 | 400 | 250 |
| 42 | 450 | 250 |
| 43 | 500 | 250 |
| 44 | 500 | 250 |
| 45 | 550 | 250 |
| 46 | 600 | 250 |
| 47 | 100 | 300 |
| 48 | 150 | 300 |
| 49 | 200 | 300 |
| 50 | 250 | 300 |
| 51 | 300 | 300 |
| 52 | 350 | 300 |
| 53 | 400 | 300 |
| 54 | 450 | 300 |
| 55 | 450 | 300 |
| 56 | 500 | 300 |
| 57 | 500 | 300 |
| 58 | 550 | 300 |
| 59 | 600 | 300 |
| 60 | 40 | 25 |

[1]Initial dosing administered to a human subject is that asymptomatic.
[2]Subsequent dosing periodically from about 6 to about 24 hours during potential exposure of at least one serotype of dengue virus.

In another aspect, the present invention relates to methods of preventing a disease resulting from a dengue invention in an child subject comprising administering to the child subject at least one initial dose of about 40 to about 600 mg of a compound of Formula (I) or a pharmaceutically acceptable salt thereof, or a pharmaceutical composition comprising about 40 to about 600 mg of a compound of Formula (I) or a pharmaceutically acceptable salt thereof, and administering to the child subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof. In further embodiments, not more than 600 mg is administered per day. In yet other embodiments, the child subject is asymptomatic at the time of administration of the at least one initial dose. In another embodiment, the subsequent doses are administered once, twice, three, four, or five times per day during potential exposure of at least one serotype of dengue virus.

Example embodiments of initial and subsequent doses combinations in a child are shown in Table 2:

TABLE 2

Dosing Regimen for a Child

| Embodiment | Initial dose (mg)[4] | Subsequent dose (mg)[5] |
|---|---|---|
| 1 | 25 | 25 |
| 2 | 50 | 25 |
| 3 | 75 | 25 |
| 4 | 100 | 25 |
| 5 | 150 | 25 |
| 6 | 200 | 25 |
| 7 | 250 | 25 |
| 8 | 300 | 25 |
| 9 | 25 | 50 |
| 10 | 50 | 50 |
| 11 | 75 | 50 |
| 12 | 100 | 50 |
| 13 | 150 | 50 |
| 14 | 200 | 50 |
| 15 | 250 | 50 |
| 16 | 300 | 50 |
| 17 | 25 | 75 |
| 18 | 50 | 75 |
| 19 | 75 | 75 |
| 20 | 100 | 75 |
| 21 | 150 | 75 |
| 22 | 200 | 75 |
| 23 | 250 | 75 |
| 24 | 300 | 75 |
| 25 | 25 | 100 |
| 26 | 50 | 100 |
| 27 | 75 | 100 |
| 28 | 100 | 100 |
| 29 | 150 | 100 |
| 30 | 200 | 100 |
| 31 | 250 | 100 |
| 32 | 300 | 100 |
| 33 | 25 | 150 |
| 34 | 50 | 150 |
| 35 | 75 | 150 |
| 36 | 100 | 150 |
| 37 | 150 | 150 |
| 38 | 200 | 150 |
| 39 | 250 | 150 |
| 40 | 300 | 150 |
| 41 | 25 | 200 |
| 42 | 50 | 200 |
| 43 | 75 | 200 |
| 44 | 100 | 200 |
| 45 | 150 | 200 |
| 46 | 200 | 200 |
| 47 | 250 | 200 |
| 48 | 300 | 200 |

[4]Initial dosing administered a human subject is that asymptomatic.
[5]Subsequent dosing periodically from about 6 to about 24 hours, or one, two, three, four, or five times per day, during potential exposure of at least one serotype of dengue virus.

In certain embodiments, the human subject is not positive for human immunodeficiency virus (HIV) infection. In other embodiments, the human subject does not have hepatitis C virus (HCV). In further embodiments, the human subject is unknown to be infected with HIV and/or HCV.

In other embodiments, the disclosed dosing regimen may be used to prevent a disease resulting from infection from a *Flavivirus* species, such as West Nile virus, yellow fever virus, and Japanese encephalitis virus. In another embodiment, the disclosed dosing regimen may be used to prevent a disease resulting from a chikungunya virus.

The human subject can be administered a compound of the present invention for a period of about between about 1 day to about 30 days. In one embodiment, the subsequent doses of a compound of Formula (I), or a pharmaceutical composition comprising a compound of Formula (I), are administered for about 5 to about 30 days. In further embodiment, the subsequent doses of a compound of Formula (I), or a pharmaceutical composition comprising a compound of Formula (I), are administered for about 30 to about 60 days. In another embodiment, the subsequent doses of a compound of Formula (I), or a pharmaceutical composition comprising a compound of Formula (I), are administered for about 60 to about 90 days. In yet another embodiment, the subsequent doses of a compound of Formula (I), or a pharmaceutical composition comprising a compound of Formula (I), are administered for about 90 to about 120 days. In another embodiment, the subsequent dose of a compound of Formula (I), or a pharmaceutical composition comprising a compound of Formula (I), is administered for about 120 to about six months.

The present invention pertains to methods of preventing a disease resulting from a dengue virus (DENV) infection in a human subject, comprising administering to the human subject at least one initial dose of about 40 to about 600 mg of a compound of Formula (I) or a pharmaceutically acceptable salt thereof, or a pharmaceutical composition comprising about 40 to about 600 mg a compound of Formula (I) or a pharmaceutically acceptable salt thereof; and administering to the human subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, wherein said subsequent doses are administered once, twice, three, or four times per day during potential exposure of at least one serotype of dengue virus, and wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

The invention is also directed to methods of preventing a disease resulting from a secondary dengue infection in a human subject, comprising administering to the human subject at least one initial dose of about 40 to about 600 mg of a compound of Formula (I) or a pharmaceutically acceptable salt thereof, or a pharmaceutical composition comprising about 40 to about 600 mg of a compound of Formula (I) or a pharmaceutically acceptable salt thereof; and administering to the human subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, wherein said subsequent doses are administered once, twice, three, or four times per day during potential exposure of at least one serotype of dengue virus, and, wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

In one embodiment of the invention, the compound of Formula (I), is a compound of Formula (II) or a pharmaceutically acceptable salt thereof. The invention also relates to methods of preventing a disease resulting from a dengue virus (DENV) infection in a human subject, comprising administering to the human subject at least one initial dose of about 40 to about 600 mg of a compound of Formula (II) or a pharmaceutically acceptable salt thereof, or a pharmaceutical composition comprising about 40 to about 600 mg of a compound of Formula (II) or a pharmaceutically acceptable salt thereof, and administering to the human subject a plurality of subsequent doses of about 25 to about 400 mg of a compound of Formula (II) or a pharmaceutically acceptable salt thereof, or a pharmaceutical composition comprising about 25 to about 400 mg of a compound of Formula (II) or a pharmaceutically acceptable salt thereof, wherein not more than 600 mg of a compound of Formula (I) is administered per day, wherein the human subject is asymptomatic at the time of administration of the at least one initial dose, and wherein said subsequent doses are administered once, twice, three, or four times per day during potential exposure of at least one serotype of dengue virus.

In another aspect, the invention relates to methods of preventing a disease resulting from a dengue virus (DENV) infection in a human subject, comprising administering orally to the human subject at least one initial dose of about 40 to about 600 mg of a compound of Formula (I) or a pharmaceutically acceptable salt thereof, or a pharmaceutical composition comprising about 40 to about 600 mg of a compound of Formula (I) or a pharmaceutically acceptable salt thereof; and administering orally to the human subject a plurality of subsequent doses of about 25 to about 400 mg of a compound of Formula (I) or a pharmaceutically acceptable salt thereof, or a pharmaceutical composition comprising about 25 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, wherein said subsequent doses are administered once, twice, three, or four times per day during potential exposure of at least one serotype of dengue virus, and, wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

In yet another aspect, the invention pertains to methods of preventing a disease resulting from a dengue virus (DENV) infection in a human subject, comprising administering to the human subject at least one initial dose of about 40 to about 600 mg of a compound of Formula (III) or a pharmaceutically acceptable salt thereof, or a pharmaceutical composition comprising about 40 to about 600 mg of a compound of Formula (III) or a pharmaceutically acceptable salt thereof; and administering to the human subject a plurality of subsequent doses of about 25 to about 400 mg of a compound of Formula (III) or a pharmaceutically acceptable salt thereof, or a pharmaceutical composition comprising about 25 to about 400 mg of a compound of Formula (III) or a pharmaceutically acceptable salt thereof, wherein not more than 600 mg of a compound of Formula (I) is administered per day, wherein the human subject is asymptomatic at the time of administration of the at least one initial dose, wherein said subsequent doses are administered once, twice, three, or four times per day during potential exposure of at least one serotype of dengue virus, and wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

In certain embodiments of the invention, the human subject is an adult or a child. In further embodiments of the invention, the plurality of human subjects may include adults or children. In some embodiments, the plurality of human subjects may include only adults. In another embodiment, the plurality of human subjects may include only children. In yet another embodiment, the plurality of human subjects may include both adults and children.

In certain embodiments of the invention, each of the plurality of human subjects may be given a different dose. In another embodiment, each of the plurality of human subjects may be given the same dose. In further embodiment, each of the plurality of human subjects may be given a variety of doses. In yet another embodiment, some of the plurality of the human subjects may be given the same dose and some of the plurality of the human subjects may be given a different dose.

In another embodiment, compound of Formula (I), the compound of Formula (II), or the compound of Formula (III) is converted to castanospermine after administration to a human subject.

In yet another embodiment, a steady state Cmin serum or plasma concentration of between about 0.05 and about 2.0 microgram/mL of castanospermine in an adult or child human subject is attained.

In one embodiment of the invention, dengue viral infection comprises at least one dengue virus selected from DENV1, DENV2, DENV3, and DENV4. In another embodiment, the dengue viral infection is secondary dengue infection. In yet another embodiment of the invention, the human subject is negative for a dengue infection using a NS1 strip assay or quantitative PCR prior to administration of at least one initial dose. In further embodiment of the invention, the virological log reduction in human subjects administered the method of prevention is at least 50% greater in persons not administered the compound or in placebo-administered groups. In yet another embodiment, administering the compound, or the pharmaceutical composition, achieves a steady state Cmin serum or plasma concentration of between about 0.4 and about 2.0 microgram/mL of castanospermine. In another embodiment of the invention, the compound, or the pharmaceutical composition, is administered intravenously, orally, rectally or sublingually.

In certain embodiments, the initial dose(s) and/or subsequent doses are each not more than 600 mg, 550 mg, 500 mg, 450 mg, 400 mg, 350 mg, 300 mg, 275 mg, 250 mg, 225 mg, 200 mg, 175 mg, 150 mg, 125 mg, 100 mg, 90 mg, 80 mg, 75 mg, 70 mg, 60 mg, 50 mg, 40 mg, or 30 mg. In other embodiments, the initial dose(s) and/or subsequent doses are each not less than 550 mg, 500 mg, 450 mg, 400 mg, 350 mg, 300 mg, 275 mg, 250 mg, 225 mg, 200 mg, 175 mg, 150 mg, 125 mg, 100 mg, 90 mg, 80 mg, 75 mg, 70 mg, 60 mg, 50 mg, 40 mg, 30 mg, or 25 mg. In certain embodiments, these upper and lower limits can be used to create a dosage range. Examples of suitable dosage ranges for the initial dose(s) and/or the subsequent doses include, but are not limited to, 25-75 mg per dose, 50-100 mg per dose, 75-125 mg per dose, 100-150 mg per dose, 150-200 mg per dose, 200-250 mg per dose, 250-300 mg per dose, 300-350 mg per dose, 350-400 mg per dose, 400-450 mg per dose, 450-500 mg per dose, 500-550 mg per dose, 550-600 mg per dose, 25-125 mg per dose, 50-150 mg per dose, 75-175 mg per dose, 100-200 mg per dose, 150-250 mg per dose, 200-300 mg per dose, 250-350 mg per dose, 300-400 mg per dose, 350-450 mg per dose, 400-500 mg per dose, 450-500 mg per dose, 500-600 mg per dose, 25-175 mg per dose, 50-200 mg per dose, 75-225 mg per dose, 100-250 mg per dose, 150-300 mg per dose, 200-350 mg per dose, 250-400 mg per dose, 300-450 mg per dose, 350-500 mg per dose, 400-550 mg per dose, 450-600 mg per dose, 25-225 mg per dose, 50-250 mg per dose, 75-275 mg per dose, 100-300 mg per dose, 150-350 mg per dose, 200-400 mg per dose, 250-450 mg per dose, 300-500 mg per dose, 350-550 mg per dose, 400-600 mg per dose, 25-275 mg per dose, 50-300 mg per dose, 75-325 mg per dose, 100-350 mg per dose, 150-400 mg per dose, 200-450 mg per dose, 250-500 mg per dose, 300-550 mg per dose, 350-600 mg per dose, 25-325 mg per dose, 50-350 mg per dose, 75-375 mg per dose, 100-400 mg per dose, 140-450 mg per dose, 200-500 mg per dose, 250-550 mg per dose, 300-600 mg per dose, 25-375 mg per dose, 50-400 mg per dose, 75-425 mg per dose, 100-450 mg per dose, 150-500 mg per dose, 200-550 mg per dose, 250-600 mg per dose, 25-425 mg per dose, 50-450 mg per dose, 75-475 mg per dose, 100-500 mg per dose, 150-550 mg per dose, 200-600 mg per dose, 25-475 mg per dose, 50-500 mg per dose, 75-525 mg per dose, 100-550 mg per dose, 150-600 mg per dose, 25-525 mg per dose, 50-550 mg per dose, 75-575 mg per dose, 100-600 mg per dose 25-550 mg per dose, 50-575 mg per dose, 75-600 mg per dose, 25-575 mg per dose, 50-600 mg per dose, or 25-600 mg per dose. In certain embodiments, these dosage ranges can be administered one or more, two or more, three or more, four or more, or five or more times as an initial dose. In other embodiments, these dosage ranges can be administered one or more, two or more, three or more, four or more, or five or more times per day as a subsequent dose. In certain embodiments of the invention, the initial dose(s) and/or the subsequent doses are administered three times per day, wherein each dose is about 167 mg to about 200 mg. In other embodiments, initial dose(s) and/or the subsequent doses are administered four times per day, wherein each dose is about 125 mg to about 150 mg. In one embodiment, the initial dose(s) and/or the subsequent doses are administered as two divided doses, wherein the total daily dose is about 225 mg to about 600 mg. In another embodiment, the initial dose(s) and/or the subsequent doses are administered as two divided doses, wherein the total daily dose is about 75 mg to about 600 mg. In other embodiments, the initial dose(s) and/or the subsequent doses are administered as two divided doses, wherein each dose is about 250 mg to about 300 mg. In yet another embodiment, the initial dose(s) and/or the subsequent doses are administered as one dose per day, wherein the total daily dose is about 40 mg to about 400 mg. In further embodiments, the initial dose(s) and/or the subsequent doses are administered as one dose per day, wherein each dose is about 225 mg to about 400 mg.

In another embodiment, the initial dose(s) and and/or subsequent doses are about 225 mg, about 240 mg, about 260 mg, about 280 mg, about 320 mg, about 340 mg, about 360 mg, about 380 mg, or about 400 mg and are administered to the human subject once a day. In other embodiments, the initial dose(s) and/or the subsequent doses are about 110 mg, about 225 mg, about 260 mg, about 280 mg, or about 300 mg and administered to the human subject twice a day. In further embodiments, the initial dose(s)

and/or the subsequent doses are about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg and are administered to the human subject three times per day. In yet other embodiments, the initial dose(s) and/or the subsequent doses are about 40 mg, about 50 mg, about 60 mg, about 70 mg, about 80 mg, about 90 mg, about 100 mg, about 110 mg, about 120 mg, about 130 mg, about 140 mg, about 150 mg and are administered to the human subject four times per day.

In one embodiment of the invention, the human subject is administered the initial dose(s) and/or the subsequent doses once per day, wherein each dose is about 3.8 mg/kg to about 6.7 mg/kg. In other embodiments, the human subject is administered the initial dose(s) and/or the subsequent doses twice per day, wherein each dose is about 4.2 mg/kg to about 5 mg/kg. In further embodiments, the human subject is administered the initial dose(s) and/or the subsequent doses three times per day, wherein each dose is about 2.8 mg/kg to about 3.33 mg/kg. In yet other embodiments, the human subject is administered the initial dose(s) and/or the subsequent doses four times per day, wherein each dose is about 2.1 mg/kg to about 2.5 mg/kg.

In one embodiment of the invention, the human subject is administered an initial dose of about 150 mg is administered a subsequent dose of about 100 mg every 6 hours for about 5 to about 30 days. In another embodiment, the human subject is administered an initial dose of about 150 mg and is administered a subsequent dose of about 100 mg every 6 hours for about 30 to about 90 days. In yet another embodiment, the human subject is administered an initial dose of about 150 mg and is administered a subsequent dose of about 100 mg every 6 hours for about 90 days to about six months. In further embodiment, the human subject is administered an initial dose of about 150 mg and is administered a subsequent dose of about 100 mg every 8 hours for about 5 to about 30 days. In certain embodiment, the human subject is administered an initial dose of about 150 mg and is administered a subsequent dose of about 100 mg every 8 hours for about 30 to about 90 days. In another embodiment, the human subject is administered an initial dose of about 150 mg and is administered a subsequent dose of about 100 mg every 8 hours for about 90 days to about six months. In yet another embodiment, the human subject is administered an initial dose of about 150 mg and is administered a subsequent dose of about 100 mg every 12 hours for about 5 to about 30 days. In another embodiment, the human subject is administered an initial dose of about 150 mg and is administered a subsequent dose of about 100 mg every 12 hours for about 30 to about 90 days. In further embodiment, the human subject is administered an initial dose of about 150 mg and is administered a subsequent dose of about 100 mg every 12 hours for about 90 days to about six months. In yet another embodiment, the human subject is administered an initial dose of about 150 mg and is administered a subsequent dose of about 150 mg every 6 hours for about 5 to about 30 days. In another embodiment, the human subject is administered an initial dose of about 150 mg and is administered a subsequent dose of about 150 mg every 6 hours for about 30 to about 90 days. In yet another embodiment, the human subject is administered an initial dose of about 150 mg and is administered a subsequent dose of about 150 mg every 6 hours for about 90 days to about six months. In another embodiment, the human subject is administered an initial dose of about 150 mg and is administered a subsequent dose of about 150 mg every 8 hours for about 5 to about 30 days. In certain embodiment, the human subject is administered an initial dose of about 150 mg and is administered a subsequent dose of about 150 mg every 8 hours for about 30 to about 90 days. In yet another embodiment, the human subject is administered an initial dose of about 150 mg and is administered a subsequent dose of about 150 mg every 8 hours for about 90 days to about six months. In one embodiment, the human subject is administered an initial dose of about 150 mg and is administered a subsequent dose of about 150 mg every 12 hours for about 5 to about 30 days. In further embodiment, the human subject is administered an initial dose of about 150 mg and is administered a subsequent dose of about 150 mg every 12 hours for about 30 to about 90 days. In yet another embodiment, the human subject is administered an initial dose of about 150 mg and is administered a subsequent dose of about 150 mg every 12 hours for about 90 days to about six months. In another embodiment, the human subject is administered an initial dose of about 150 mg and is administered a subsequent dose of about 200 mg every 6 hours for about 5 to about 30 days. In one embodiment, the human subject is administered an initial dose of about 150 mg and is administered a subsequent dose of about 200 mg every 6 hours for about 30 to about 90 days. In another embodiment, the human subject is administered an initial dose of about 150 mg and is administered a subsequent dose of about 200 mg every 6 hours for about 90 days to about six months. In further embodiment, wherein the human subject is administered an initial dose of about 150 mg and is administered a subsequent dose of about 200 mg every 8 hours for about 5 to about 30 days. In yet another embodiment, the human subject is administered an initial dose of about 150 mg and is administered a subsequent dose of about 200 mg every 8 hours for about 30 to about 90 days. In one embodiment, the human subject is administered an initial dose of about 150 mg and is administered a subsequent dose of about 200 mg every 8 hours for about 90 days to about six months. In another embodiment, the human subject is administered an initial dose of about 150 mg and is administered a subsequent dose of about 200 mg every 12 hours for about 5 to about 30 days. In further embodiment, the human subject is administered an initial dose of about 150 mg and is administered a subsequent dose of about 200 mg every 12 hours for about 30 to about 90 days. In another embodiment, the human subject is administered an initial dose of about 150 mg and is administered a subsequent dose of about 200 mg every 12 hours for about 90 days to about six months. In certain embodiment, the human subject is administered an initial dose of about 200 mg and is administered a subsequent dose of about 100 mg every 6 hours for about 5 to about 30 days. In yet another embodiment, the human subject is administered an initial dose of about 200 mg and is administered a subsequent dose of about 100 mg every 6 hours for about 30 to about 90 days. In another embodiment, the human subject is administered an initial dose of about 200 mg and is administered a subsequent dose of about 100 mg every 6 hours for about 90 days to about six months. In one embodiment, the human subject is administered an initial dose of about 200 mg and is administered a subsequent dose of about 100 mg every 8 hours for about 5 to about 30 days. In further embodiment, the human subject is administered an initial dose of about 200 mg and is administered a subsequent dose of about 100 mg every 8 hours for about 30 to about 90 days. In yet another embodiment, the human subject is administered an initial dose of about 200 mg and is administered a subsequent dose of about 100 mg every 8 hours for about 90 days to about six months. In another embodiment, the human subject is administered an initial dose of about 200 mg and is administered a subsequent dose of about 100 mg every 12 hours for about 5 to about 30 days. In one embodiment, the human subject is administered an initial dose of about 200 mg and is administered a subsequent dose of about 100 mg every 12 hours for about 30 to about 90 days. In another embodiment, the human subject is administered an initial dose of about 200 mg and is administered a subsequent dose of about 100 mg every 12 hours for about 90 days to about six months. In further embodiment, the human subject is administered an initial dose of about 200 mg and is administered a subsequent dose of about 150 mg every 6 hours for about 5 to about 30 days. In another embodiment of the invention, the human subject is administered an initial dose of about 200 mg and is administered a subsequent dose of about 150 mg every 6 hours for about 30 to about 90 days. In yet another embodiment, the human subject is administered an initial dose of about 200 mg and is administered a subsequent dose of about 150 mg every 6 hours for about 90 days to about six months. In another embodiment, the human subject is administered an initial dose of about 200 mg and is administered a subsequent dose of about 150 mg every 8 hours for about 5 to about 30 days. In one embodiment, the human subject is administered an initial dose of about 200 mg and is administered a subsequent dose of about 150 mg every 8 hours for about 30 to about 90 days. In yet another embodiment, the human subject is administered an initial dose of about 200 mg and is administered a subsequent dose of about 150 mg every 8 hours for about 90 days to about six months. In another embodiment, the human subject is administered an initial dose of about 200 mg and is administered a subsequent dose of about 150 mg every 12 hours for about 5 to about 30 days. In another embodiment, the human subject is administered an initial dose of about 200 mg is administered a subsequent dose of about 150 mg every 12 hours for about 30 to about 90 days. In an embodiment of the invention, the human subject is administered an initial dose of about 200 mg and is administered a subsequent dose of about 150 mg every 12 hours for about 90 days to about six months. In further embodiment, the human subject is administered an initial dose of about 200 mg and is administered a subsequent dose of about 200 mg every 6 hours for about 5 to about 30 days. In yet another embodiment, the human subject is administered an initial dose of about 200 mg and is administered a subsequent dose of about 200 mg every 6 hours for about 30 to about 90 days. In another embodiment, the human subject is administered an initial dose of about 200 mg is administered a subsequent dose of about 200 mg every 6 hours for about 90 days to about six months. In an embodiment of the invention, the human subject is administered an initial dose of about 200 mg and is administered a subsequent dose of about 200 mg every 8 hours for about 5 to about 30 days. In further embodiment, the human subject is administered an initial dose of about 200 mg and is administered a subsequent dose of about 200 mg every 8 hours for about 30 to about 90 days. In yet another embodiment, the human subject is administered an initial dose of about 200 mg and is administered a subsequent dose of about 200 mg every 8 hours for about 90 days to about six months. In another embodiment, the human subject is administered an initial dose of about 200 mg and is administered a subsequent dose of about 200 mg every 12 hours for about 5 to about 30 days. In an embodiment of the invention, the human subject is administered an initial dose of about 200 mg and is administered a subsequent dose of about 200 mg every 12 hours for about 30 to about 90 days.

In one embodiment, the human subject is administered an initial dose of about 200 mg and is administered a subsequent dose of about 200 mg every 12 hours for about 90 days to about six months. In another embodiment, the human subject is administered a single or a divided dose of about 25 to about 400 mg of the compound or the pharmaceutical composition, for about between about 5 days to about one year. In yet another embodiment, the human subject is administered a divided dose of about 25 to about 400 mg of the compound, or the pharmaceutical composition, for about between about 5 days to about one year.

The compounds of the present invention can be administered in a single or a divided dose. In one embodiment, the human subject is administered a divided dose of about 25 to about 400 mg of a compound of Formula (I), or a pharmaceutical composition comprising a compound of Formula (I), for about between about 5 days to about 30 days. In another embodiment, the human subject is administered a single dose of about 25 to about 100 mg of a compound of Formula (I), or a pharmaceutical composition comprising a compound of Formula (I), for about between about 5 days to about six months.

Compounds of Formula (I) and Formula (II) inhibit the replication of a variety of laboratory and clinical dengue strains of DENV1-4, with submicromolar $EC_{50}$ values. As used herein, "$EC_{50}$" refers to the concentration of an antiviral that produces 50% of the maximal possible antiviral effect. In one embodiment, the method of the invention is used to prevent a disease resulting from an infection caused by at least one dengue virus selected from DENV1, DENV2, DENV3, and DENV4.

The method of the present invention is used to prevent a disease resulting from a dengue viral infection in a subject who has tested negative for a dengue virus. Known methods for diagnosis of dengue viral infection can be used including, but not limited to, an NS1 strip assay or a quantitative PCR assay.

In one embodiment, the human subject tests negative for a dengue infection in a NS1 strip assay. In another embodiment, the human subject tests negative for a dengue infection in a quantitative PCR assay.

The compounds of the present invention can be administered intravenously, orally, rectally, or sublingually. Intravenous, oral, rectal and sublingual dosing can be in a single or divided dose. Intravenous dosing can also be a slow infusion over a period of time and the slow infusions can be constant or intermittent.

The compounds of the invention can be administered several times a day or as needed to maintain a steady Cmin serum concentration of between about 0.05 and about 2.0 microgram/mL. A suitable interval between the two administrations includes any time period which maintains a therapeutically effective plasma level of a compound of Formula (I). Such an interval can be, for example, about 12 hours. In one embodiment, the human subject is administered a compound of Formula (I) or a compound of Formula (II) twice a day. Dosing at intervals is intended to cover subsequent dosing, either as a single or a divided dose, routinely during the course of therapy. For example, dosing can be about every 6 to about 12 hours during the course of the method, but it is intended to cover the possibility that a dose may have been missed during at least one interval. In another embodiment, the human subject is administered a compound of Formula (I) or a compound of Formula (II) three times a day. In yet another embodiment, the human subject is administered a compound of Formula (I) or a compound of Formula (II) four times a day.

As such, a first dose can be administered at 6 am on Day 1 and a second dose can be administered at 6 pm on Day 1 for a total of two doses in a 24 hour period or day. Further, a first dose can be administered at 12 am on Day 1, a second dose can be administered at 6 am on Day 1, a third dose can be administered at 12 pm on Day 1, and a fourth dose can be administered at 6 pm on Day 1 for a total of four doses in a 24 hour period or day. In one embodiment, the therapeutically effective plasma level is the level at which the Cmin concentration of a compound of Formula (I) is achieved.

The invention also relates to a method of preventing a disease resulting from a dengue virus infection by achieving a steady state Cmin serum or plasma concentration of between about 0.05 and about 2.0 microgram/mL of castanospermine in an adult or child human subject. As used herein, "Cmin" refers to the minimum concentration that a drug achieves after the drug has been administered and prior to the administration of a second or additional dose. Steady state Cmin is achieved when the overall intake of a drug Cmin concentration is fairly in dynamic equilibrium with its elimination. In some embodiments, Cmin concentration of castanospermine is determined at one or more points following administration with techniques known in the art.

It is known that a steady state minimum castanospermine concentration of 400 nanograms/ml is associated with a 50 mg/kg BID dose in mice and that the antiviral effect of celgosivir in vivo seems to be correlated with the minimum steady state concentration of castanospermine (Watanabe et al). Literature also shows that the pharmacokinetics of celgosivir is linear with dose over the tolerated dose range (Sorbera et al). International Publication No. WO 2014/143907 discloses pharmacokinetic parameters for castanospermine for the CELADEN study. Pharmacokinetic simulations using those pharmacokinetic parameters suggest that a 4× daily dose of 150 mg should produce a steady state minimum concentration of 1469 nanograms/ml, that a 3× daily dose of 200 mg results in an 799 nanograms/ml steady state minimum concentration of castanospermine, and that 300 mg twice daily results in a steady state minimum concentrations of castanospermine of 532 ng/ml. Extrapolating linearly, therefore, the minimum protective dose (achieving 400 nanograms/ml steady state minimum) is approximately 40 mg every 6 h, 75 mg every 8 h and 225 mg every 12 h. Further, WO 2014/143907 discloses that the CELADEN study regimen produce a steady state maximum castanospermine concentration of 5100 nanograms/ml. The adverse event profile in that study showed a higher incidence of GI effects, but not increased severity at that dose. That study also showed that in theory the maximum daily dose can be as high as 600 mg as a total dose, or 400 mg as a single dose, confirming literature to this effect. The FDA has published generic scaling factors to adjust mg/kg dosing in animals to mg/kg dosing in humans. Generically for mice, that scaling factor is 12. Therefore, 50 mg/kg BID is equivalent to a dose of 4.2 mg/kg BID in humans, which for a 60 kg human is equivalent to 250 mg. The same dose administered three or four times daily is equivalent to 167 mg and 125 mg and 2.8 and 2.1 mg/kg respectively. In a 60 kg human, the maximum single dose is 6.7 mg/kg, and the maximum daily dose is 10 mg/kg.

In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.4 microgram/mL of castanospermine. In another embodiment, the steady state Cmin serum or plasma concentration achieved in an adult or child subject is between about 0.4 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In one embodiment, the minimum steady state concentration of castanospermine achieved exceeds 0.4 microgram/mL during administration of the initial dose(s) and/or subsequent doses to the human subject. In further embodiments, the minimum steady state concentration of castanospermine achieved exceeds 0.5 microgram/mL during administration of the initial dose(s) and/or subsequent doses to the human subject. In yet other embodiments, the minimum steady state concentration of castanospermine achieved exceeds 0.6 microgram/mL during administration of the initial dose(s) and/or subsequent doses to the human subject. In another embodiment, the minimum steady state concentration of castanospermine achieved exceeds 0.7 microgram/mL during administration of the initial dose(s) and/or subsequent doses to the human subject. In still other embodiments, the minimum steady state concentration of castanospermine achieved exceeds 0.8 microgram/mL during administration of the initial dose(s) and/or subsequent doses to the human subject. In other embodiments, the minimum steady state concentration of castanospermine achieved exceeds 0.9 microgram/mL during administration of the initial dose(s) and/or subsequent doses to the human subject. In yet another embodiment, the minimum steady state concentration of castanospermine achieved exceeds 1.0 microgram/mL during administration of the initial dose(s) and/or subsequent doses to the human subject. In some embodiments, the minimum steady state concentration of castanospermine achieved exceeds 1.1 microgram/mL during administration of the initial dose(s) and/or subsequent doses to the human subject. In another embodiment, the minimum steady state concentration of castanospermine achieved exceeds 1.2 microgram/mL during administration of the initial dose(s) and/or subsequent doses to the human subject. In yet another embodiment, the minimum steady state concentration of castanospermine achieved exceeds 1.3 microgram/mL during administration of the initial dose(s) and/or subsequent doses to the human subject. In still other embodiments, the minimum steady state concentration of castanospermine achieved exceeds 1.4 microgram/mL during administration of the initial dose(s) and/or subsequent doses to the human subject. In yet other embodiments, the minimum steady state concentration of castanospermine achieved does not exceed 2.0 microgram/mL during administration of the initial dose(s) and/or subsequent doses to the human subject.

The invention further relates to a method of preventing a disease resulting from a dengue virus infection by achieving an average steady state Cmin serum or plasma concentration of between about 0.05 and about 2.0 microgram/mL of castanospermine in a plurality of human subjects after the administration of the compounds of the invention. The average steady state Cmin of the plurality of human subjects is calculated as an average of steady state Cmin serum or plasma concentrations from each of the plurality of human subjects. In certain embodiments of the invention, an average steady state Cmin serum or plasma concentration of between about 0.05 and about 2.0 microgram/mL of castanospermine in the plurality of human subjects is attained after administration of the compound of the invention.

In one embodiment, the average steady state Cmin serum or plasma concentration achieved in the plurality of human subjects is between about 0.08 and about 0.5 microgram/mL of castanospermine. In another embodiment, the average steady state Cmin serum or plasma concentration achieved in the plurality of human subjects is between about 0.05 and about 0.08 microgram/mL of castanospermine. In yet another embodiment, the average steady state Cmin serum or plasma concentration achieved in the plurality of human subjects is between about 0.08 and about 0.11 microgram/mL of castanospermine. In a further embodiment, the average steady state Cmin serum or plasma concentration achieved in the plurality of human subjects is between about 0.11 and about 0.4 microgram/mL of castanospermine. In another embodiment, the average steady state Cmin serum or plasma concentration achieved in the plurality of human subjects is between about 0.4 and about 0.75 microgram/mL of castanospermine. In further embodiment, the average steady state Cmin serum or plasma concentration achieved in the plurality of human subjects is between about 0.75 and about 1.0 microgram/mL of castanospermine. In yet another embodiment, the average steady state Cmin serum or plasma concentration achieved in the plurality of human subjects is between about 1.0 and about 2.0 microgram/mL of castanospermine. In another embodiment, the average steady state Cmin serum or plasma concentration achieved in the plurality of human subjects is between about 1.0 and about 1.5 microgram/mL of castanospermine. In further embodiment, the average steady state Cmin serum or plasma concentration achieved in the plurality of human subjects is between about 1.5 and about 2.0 microgram/mL of castanospermine. In yet another embodiment, the average steady state Cmin serum or plasma concentration achieved in the plurality of human subjects is between about 1.25 and about 1.75 microgram/mL of castanospermine.

In another aspect, methods of the present invention can prevent a disease resulting from a secondary dengue infection or an "antibody enhanced" (ADE) dengue infection. A "secondary" infection refers to a DENV infection in a patient who was previously infected with DENV. An "antibody enhanced" infection refers to a DENV infection made more severe due to a prior infection with one of the four DENV serotypes. Ninety percent (90%) of severe and potentially fatal dengue diseases, such as dengue hemorrhagic fever (DHF) or dengue shock syndrome (DSS) are caused by a secondary dengue infection. In secondary dengue infection, prior infection causes generation of an antibody that takes on a pathogenic role. Upon reinfection with DENV, the antibody response triggers a systemic inflammatory reaction resulting in vascular leakage. In one embodiment, the dengue viral infection is a secondary dengue infection.

In another aspect of the invention, viral load reduction of a human subject administered the compound is at least 50% greater than in persons not administered the compound or in placebo-administered groups. As used herein, the term "viral load" refers to the amount of virus in the blood stream of a human subject. The viral load is measured before administration of the first dose and then at various time intervals after administration. The dose amounts can be adjusted to increase the viral load reduction or if no viral reduction is observed at a specific dose it can be adjusted to promote viral reduction.

In one embodiment, the virological log reduction in human subjects administered with a compound of Formula (I) is at least about 50% greater than in persons not administered the compound or in placebo-administered groups. In another embodiment, the virological log reduction in human subjects administered with a compound of Formula (I) is between about 60% to 70% greater than in persons not administered the compound or in placebo-administered groups. In another embodiment, the virological log reduction in human subjects administered with a compound of Formula (I) is between about 70% to 80% greater than in persons not administered the compound or in placebo-administered groups. In yet another embodiment, the virological log reduction in human subjects administered with a compound of Formula (I) is between about 80% to 90% greater than in persons not administered the compound or in placebo-administered groups.

EXAMPLES

Figure 7:
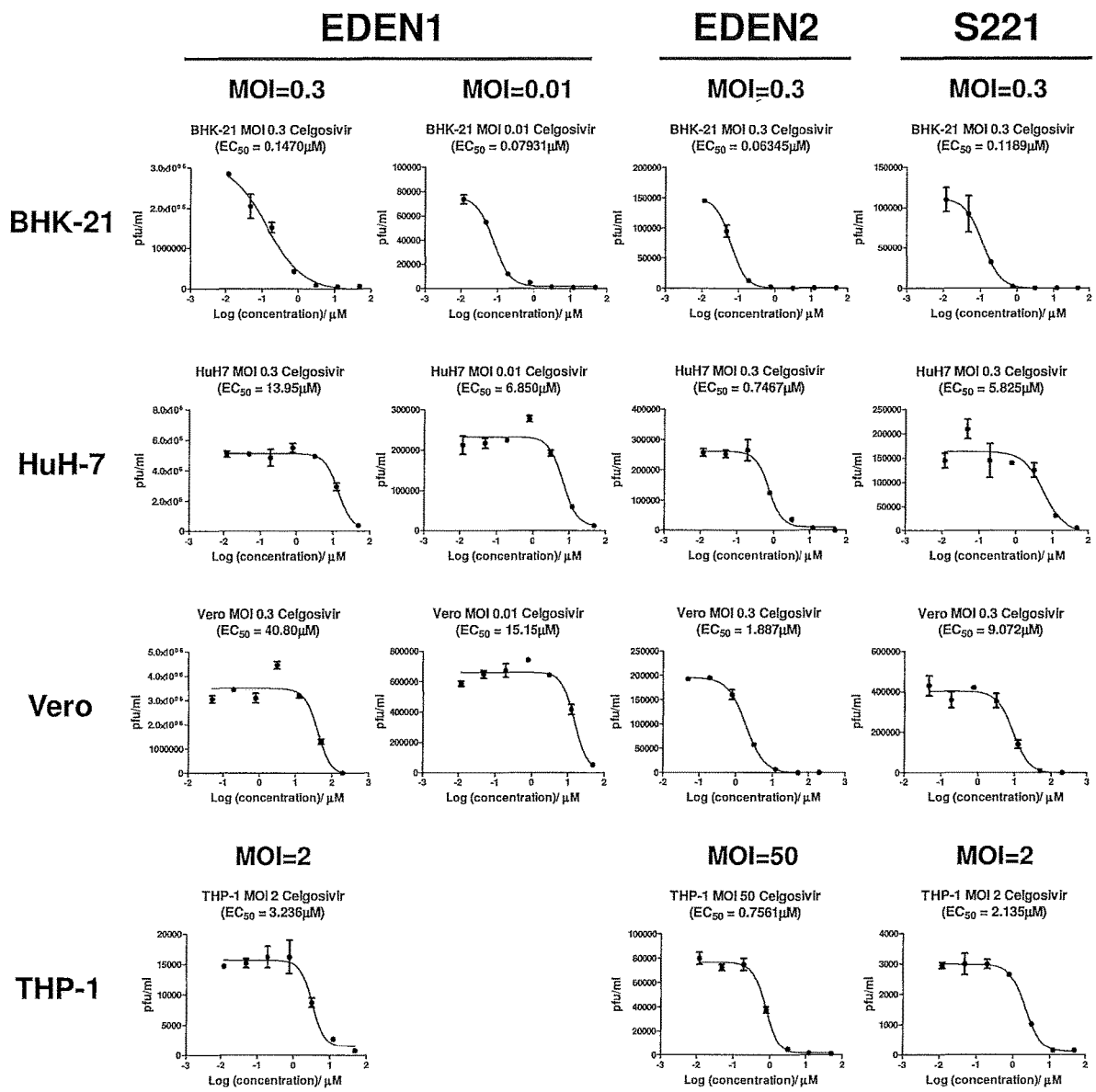
FIG. 7 the antiviral effect of celgosivir against EDEN1, EDEN2, and S221 in BHK-21, HuH-7, Vero, and THP-1 cells. Cells were infected with DENV strains for 1 hour at 37° C. and washed once with culture media. Cells were then incubated for additional 48 hours in culture media containing celgosivir or NITD008 with a serial 4-fold dilution from 200 μM or 50 μM. The supernatants were subjected to standard plaque assay and the $EC_{50}$ values were determined using the GraphPad Prism software. Experiments were conducted in duplicate (except on THP-1 cells) and the graphs show the representative for the celgosivir administrations.

Example 1: The In Vitro Efficacy of Celgosivir is Modulated by Different Cell Lines and Viral Strains BHK-21 cells (baby hamster kidney cell line), HuH7 cells (human hepatocyte cell line), and Vero cells (African green monkey kidney cell line), known as a type-I IFN-deficient cell type (Desmyter et al., 1968) were used to test the antiviral effect of celgosivir and were infected with EDEN1 (clinical DENV1 isolate), EDEN2 (clinical DENV2 isolate), or S221 (mouse-adapted DENV2 strain) at MOI of 0.3 and virus titer in the supernatant at 48 hours post-infection (pi) was used to determine $EC_{50}$ of celgosivir. The effect of celgosivir against Ab-mediated infection using THP-1 cells with enhancing concentration of 4G2 Ab was also analyzed. NITD008, an adenosine analog inhibitor of DENV polymerase (Yin et al., 2009) was used as a positive control. The $EC_{50}$ of celgosivir in HuH-7 cells was found to be different among the virus strains, and was higher for EDEN1 (17.4 μM) and S221 (5.1 μM) than EDEN2 171 (0.82 μM) (Table 3 and FIG. 7). In contrast $EC_{50}$ values of celgosivir in BHK-21 cells (baby hamster kidney cell line) was below 0.2 μM against all virus strains (Table 3) similar to the observation reported elsewhere (e.g., see Rathore et al.). Since virus titer in the supernatant of EDEN1 infection was more than 10-fold higher than EDEN2 or S221, MOI of 0.01 was used for EDEN1 to obtain similar level of virus titer to EDEN2 or S221 (FIG. 7). The $EC_{50}$ of celgosivir against EDEN1 was 6.0 μM in HuH-7 cells, which was comparable to S221 but nevertheless still higher than EDEN2 infection at MOI of 0.3 (Table 3 and FIG. 7), indicating that celgosivir is more effective against EDEN2 than EDEN1 or S221 in HuH-7 cells, but not in BHK-21 cells. Since BHK-21 cell line is thought to be defective in interferon (IFN) production (MacDonald et al., 2007), Vero cells (African green monkey kidney cell line), known as a type-I IFN-deficient cell type (Desmyter et al., 1968), were also tested with celgosivir administration. The $EC_{50}$ values of celgosivir were reproducibly higher against EDEN1 (51.0 μM and 13.8 μM at MOI of 0.3 and 0.01, respectively) and S221 (8.3 μM at MOI of 0.3) compared with EDEN2 (2.4 mM at MOI of 0.3) (Table 3 and FIG. 7), suggesting that type-I IFN production is probably not responsible for the virus strain-dependent sensitivity to celgosivir. We further examined the effect of celgosivir against Ab-mediated infection using THP-1 cells with enhancing concentration of 4G2 Ab. Celgosivir was also less effective against EDEN1 (3.2 μM at MOI of 2) and S221 (2.1 μM at MOI of 2) than EDEN2 (0.8 μM at MOI of 50) (Table 3). Notably, the effect of the directly acting antiviral NITD008 is fairly consistent among the virus strains in each cell line (Table 3).

TABLE 3

Antiviral effect of celgosivir and NITD008 against DENV strains in BHK-21, Huh-7, Vero and THP-1 cells.

| | | | $EC_{50}$ (SD) | |
|---|---|---|---|---|
| Cell line | virus | MOI | Celgosivir | NITD008 |
| BHK-21 | EDEN1 | 0.3 | 0.105 (0.059) | 0.865 (0.172) |
| | | 0.01 | 0.066 (0.019) | 0.608 (0.139) |
| | EDEN2 | 0.3 | 0.061 (0.003) | 0.354 (0.157) |
| | S221 | 0.3 | 0.119 (0.000) | 0.509 (0.285) |
| HuH-7 | EDEN1 | 0.3 | 17.430 (4.921) | 0.684 (0.019) |
| | | 0.01 | 5.961 (1.258) | 0.356 (0.058) |
| | EDEN2 | 0.3 | 0.824 (0.109) | 0.098 (0.058) |
| | S221 | 0.3 | 5.093 (1.036) | 0.074 (0.008) |
| Vero | EDEN1 | 0.3 | 51.035 (14.47) | 2.815 (0.069) |
| | | 0.01 | 13.805 (1.902) | 0.910 (0.223) |
| | EDEN2 | 0.3 | 2.434 (0.773) | 1.174 (0.066) |
| | S221 | 0.3 | 8.336 (1.041) | 1.477 (0.047) |
| THP-1 | EDEN1 | 2 | 3.236 (—) | 0.358 (—) |
| | EDEN2 | 50 | 0.756 (—) | 0.679 (—) |
| | S221 | 2 | 2.135 (—) | 0.390 (—) |

Experiment was conducted in duplicate and the results show the average $Ec_{50}$ values with standard deviations (SD).
Data on THP-1 cells were obtained from a single experiment and shown without SD.

Figure 2:
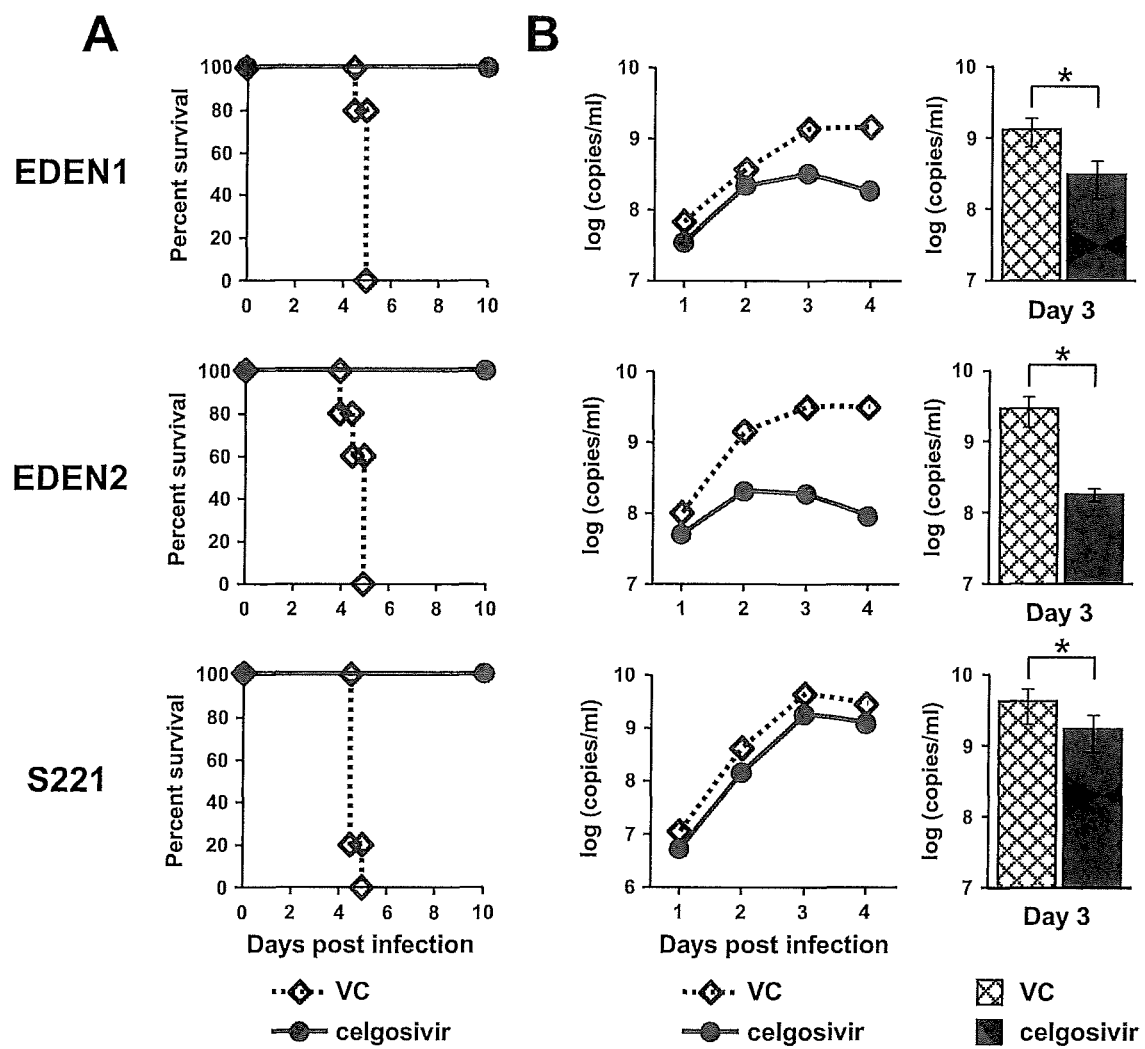
FIG. 2 shows administration of celgosivir at 50 mg/kg BID against lethal infection of EDEN1, EDEN2 and S221. AG129 mice were pre-injected i.p. with 50 μg (for EDEN1 and EDEN2) or 10 μg (for S221) 4G2 Ab followed by next day inoculation i.v. with EDEN1 ($7 \times 10^7$ pfu), EDEN2 ($1 \times 10^8$ pfu) or S221 ($2 \times 10^4$ pfu). Administration of celgosivir at 50 mg/kg BID was started at the time of infection (on day 0). (A) Mouse survival rate was monitored by day 10 pi. (B) Blood samples were collected on day 1-4 pi and mixed serum from each group were subjected to real-time RT PCR to obtain the average viral genome copy numbers (left panels). Viral copy number on day 3 pi was measured individually and the graphs show the average results with standard deviations (right panels). A P value less than 0.05 was considered significant (*P<0.05). The number of mice per group is 5.
Figure 3:
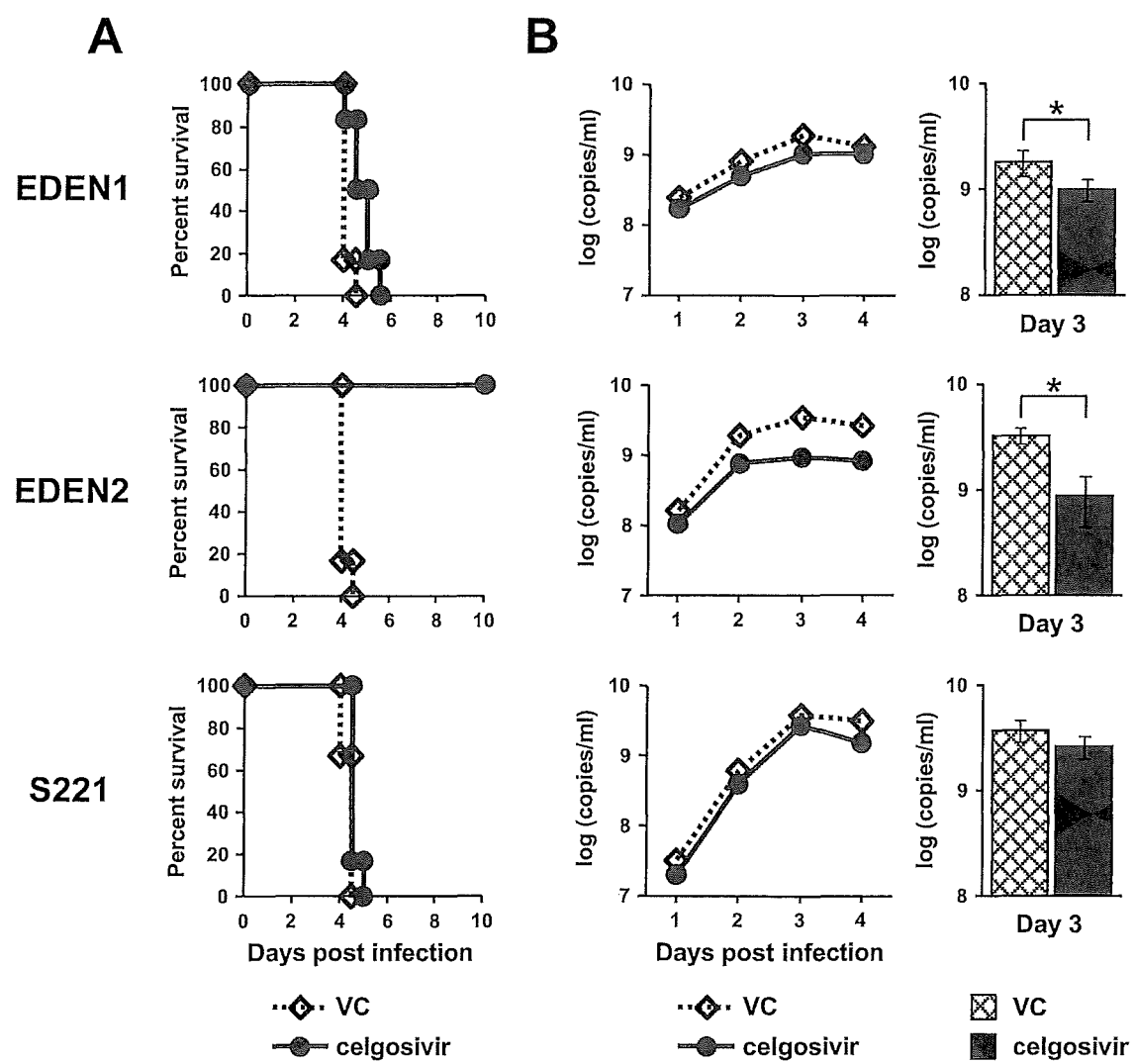
FIG. 3 show administration of celgosivir at 10 mg/kg BID against lethal infection of EDEN1, EDEN2 and S221. AG129 mice were pre-injected i.p. with 4G2 Ab followed by next day inoculation i.v. with EDEN1, EDEN2 or S221 as described above. Administration of celgosivir at 10 mg/kg BID was started on day 0. (A) Mouse survival rate was monitored by day 10 pi. (B) Blood samples were collected on days 1-4 pi and mixed serum from each group were subjected to real-time RT PCR to obtain the average viral genome copy numbers (left panels). Viral copy number on day 3 pi was measured individually and the graphs show the average results with standard deviations (right panels). A P value less than 0.05 was considered significant (*P<0.05). The number of mice per group is 6.

Example 2: Celgosivir has a Different Antiviral Efficacy Among Virus Strains in Mice AG129 mouse models of clinical DENV strains, EDEN1 and EDEN2, in addition to mouse-adapted S221 strain were developed. To increase infection level in mice, high virus titer of EDEN1 ($7 \times 10^7$ pfu) and EDEN2 ($1 \times 10^8$ pfu) were inoculated intravenously (iv) into AG129 mice. These virus titers did not induce mortality (FIG. 1A), although high levels of viremia could be detected over 8 days after infection (FIG. 1B). However when the infections were carried under ADE conditions, 100% mortality was observed by day 5 pi (FIG. 1A) for both EDEN1 and EDEN 2. The peak viremia was enhanced in the ADE infection (FIG. 1B), as was the level of serum cytokines such as TNFα and IL-6 (FIG. 1C), which was more prominent for the ADE infection with clinical isolates. To test the in vivo efficacy of celgosivir, mice were orally administered 50 mg/kg twice-daily (BID) starting at the time of infection. As shown in FIG. 2A, this dosing regimen completely protected mice from lethal infection against all 3 virus strains. On the other hand, viremia data on day 3 pi showed a different efficacy of celgosivir among the virus strains, with 4.3-fold (P=0.0051), 16.5-fold (P=0.0018) and 2.4-fold (P=0.0496) lower viremia level in the mice administered celgosivir than vehicle control (VC) mice for EDEN1, EDEN2 and S221, respectively (FIG. 2B). This indicates that celgosivir is more effective against EDEN2 than EDEN1 or S221 in mice similar to the observation in cell-based assays using HuH-7, Vero and THP-1 cells but not in BHK-21 cells (Table 3). To extend this observation, we also tested dosing 10 mg/kg BID from the time of infection in mice. Although this concentration could not protect mice from death against EDEN1 and S221, it was still 100% protective against EDEN2 infection (FIG. 3A). Interestingly, although the administration for S221 did not induce significant viremia suppression (1.4-fold; P=0.1312), the viremia reduction for EDEN1 and EDEN2 on day 3 was observed to be significantly lower in mice administered celgosivir than VC (1.8-fold; P=0.0058 and 3.7-fold; P=0.0004, respectively) (FIG. 3B). Thus, celgosivir administration even the dose of 10 mg/kg BID can induce significant levels of viremia reduction against EDEN1 and EDEN2 when the administration is started at the time of infection, an observation that may have potential clinical implication for dengue prophylaxis.

Figure 4:
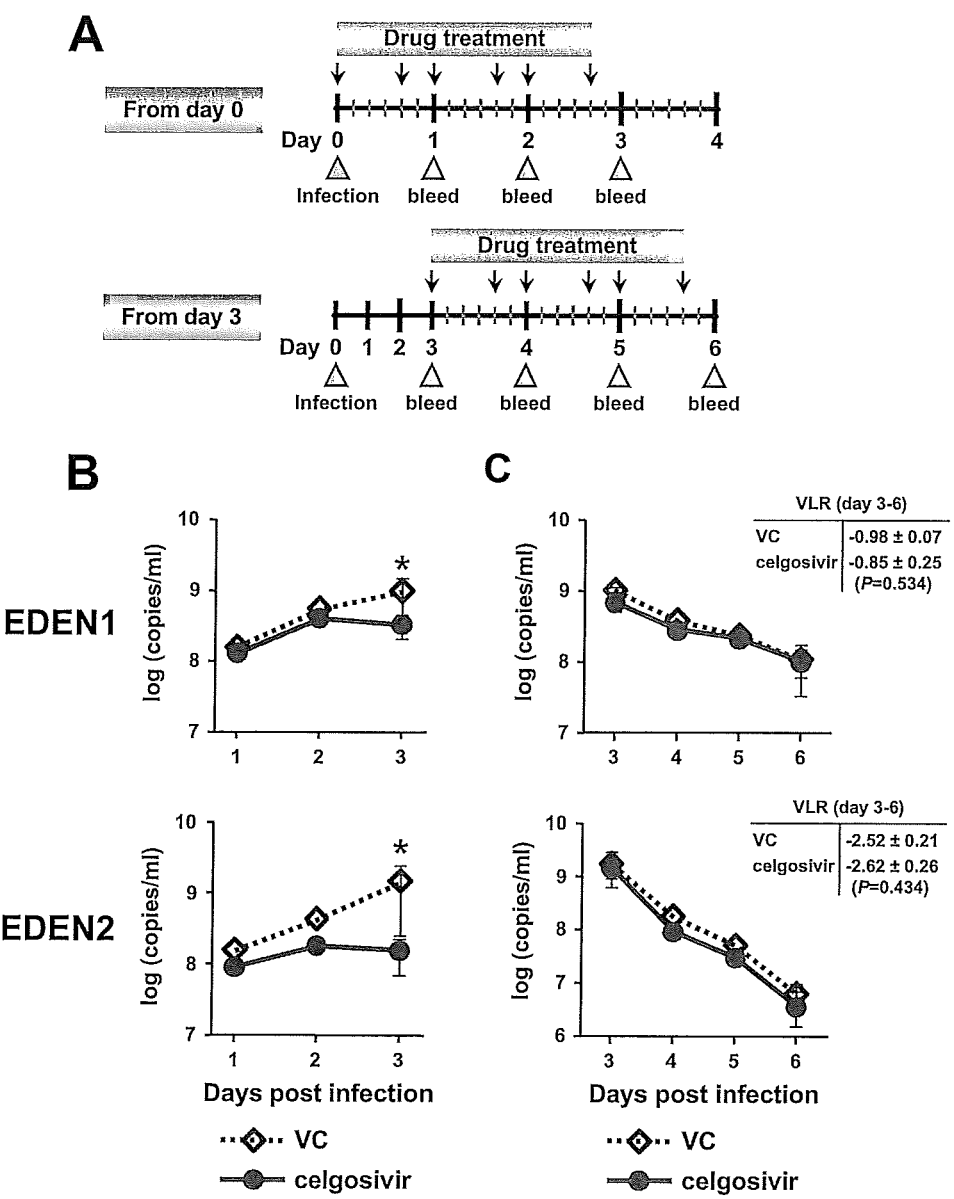
FIG. 4 shows administration of celgosivir at 50 mg/kg BID starting from day 0 or day 3. Mice were inoculated i.v. with EDEN1 ($7 \times 10^7$ pfu) or EDEN2 ($1 \times 10^8$ pfu). (A) A regimen for celgosivir administration starting at the time of infection (day 0) or peak viremia level (day 3) was illustrated. (B) Celgosivir administration was started on day 0 and serum samples were collected on day 1-3 pi. Average viral copy numbers on day 1 and 2 were measured using mixed serum of each group. Viral copy number on day 3 was measured individually and the graphs show the average results with standard deviations. A P value less than 0.05 was considered significant (*P<0.05). The number of mice per group is 6. (C) Celgosivir administration was started on day 3 and serum samples were collected on day 3-6 pi. Average viral copy numbers on days 4 and 5 were measured using mixed serum of each group. Viral copy number on days 3 and 6 was measured individually and shown in the graphs as the average results with standard deviations. The virological log reduction (VLR) from day 3 to day 6 was also shown as the mean value and standard deviations. The number of mice per group is 6.
Figure 5:
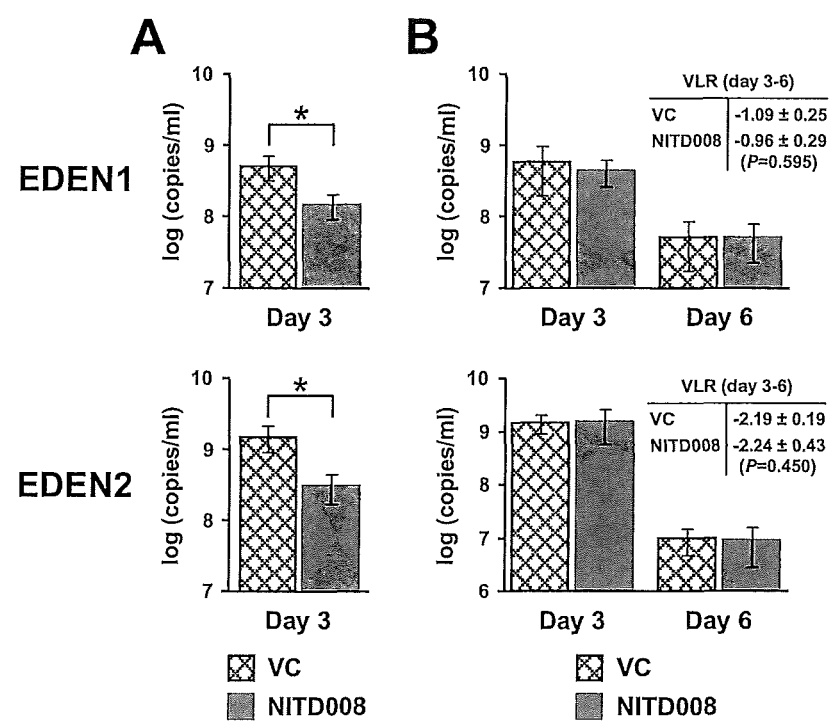
FIG. 5 shows administration of NITD008 at 25 mg/kg BID starting from day 0 or day 3 post-infection in the non-lethal mouse model a schematic of the dosing conducted in the DENV2 infected mice in a lethal ADE model of viremia.

Example 3: Antiviral Efficacy when Administration is Commenced During Peak Viremia Becomes Less Prominent in Mice Our in vivo data showed that the clinical strains examined in this study have a better sensitivity to celgosivir compared with S221 that has been used for the drug evaluation (Rathore et al., 2011; Watanabe et al., 2012a). Nevertheless celgosivir seems less effective in humans even for DENV2-infected trial subjects (Low et al., 2014). Since dengue fever patients in general present at a clinic when viremia is at a peak level (Low et al., 2014; Nguyen et al., 2013; Tricou et al., 2010), we next compared the 2 different dosing regimens; one started at the time of infection and another started at the time of peak viremia (on day 3 pi) similar to human situation (FIG. 4A). In this experiment, we used a non-lethal viremia mouse model, which permits the tracking of viremia kinetics for a longer period of time (FIG. 1B). When mice were administered celgosivir from the time of infection, viremia on day 3 pi showed significant levels of viremia reduction, with 2.9-fold for EDEN1 (F=0.0159) and 9.0-fold for EDEN2 (P=0.0235) (FIG. 4B). Surprisingly, however, when treatment was started at the time of peak viremia, log reduction of viremia (VLR) from day 3 to day 6 in the treated mice was 0.85 for EDEN1 with no superiority to VC (0.98) (P=0.534) and 2.62 for EDEN2 also with no remarkable reduction compared with VC (2.52) (P=0.434) (FIG. 2C). Thus, celgosivir did not induce significant viremia reduction if the administration was started at the time of peak viremia, even though up to 9-fold reduction of peak viremia was inducible when the administration was started from the time of infection. In order to address whether the observed phenomenon was because celgosivir targeted a host enzyme, we examined the efficacy of NITD008 at 25 mg/kg BID in mice infected with EDEN1 or EDEN2. Administration of NITD008 from day 0 induced significant viremia reduction on day 3 pi, with 3.5-fold (P=0.0101) and 4.9-fold (P=0.0017) for EDEN1 and EDEN2, respectively (FIG. 5A). However, VLR from day 3 to day 6 reproducibly showed no significant differences between VC and NITD008 administration; 1.09 (VC) and 0.96 (NITD008) for EDEN1 (P=0.595), and 2.19 (VC) and 2.24 (NITD008) for EDEN2 CP=0.450) (FIG. 5B). Taken together, these results suggest that the antiviral effect on controlling viremia becomes less prominent once viremia reaches the peak level irrespective of whether the drug acts through a host target or directly against a viral target.

Figure 6:
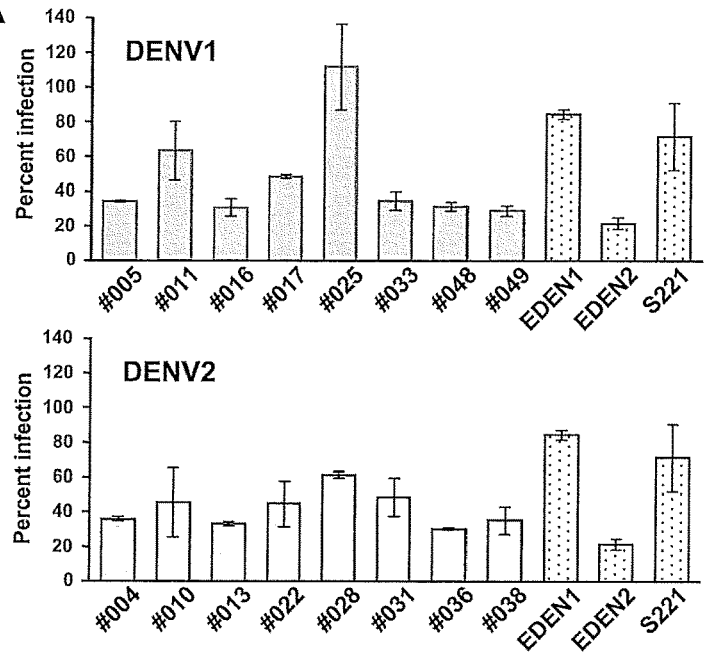
FIG. 6 shows the efficacy of celgosivir against clinical DENV strains obtained from CELADEN trial patients. (A) Total 16 clinical DENV strains from CELADEN trial (8 from either DENV1 or DENV2 infected patients) were used for infection in HuH-7 cells in the absence or presence of celgosivir at the concentration of 3 μM. EDEN1, EDEN2 and S221 were used as control virus strains. The MOI of each strain was indicated in supplementary FIG. 2. After 48 hours pi, virus titer in the supernatants was determined by standard plaque assay using BHK-21 cells. The percentages of virus titer were calculated based on virus infection control of each strain. Error bars indicate standard deviations from duplicate experiments. (B and C) Mice were inoculated i.v. with DENV2 strains, #031 ($2 \times 10_7$ pfu), #013 ($1 \times 10_7$ pfu) or #036 ($2 \times 10_7$ pfu). (B) Administration of celgosivir at 50 mg/kg BID was started on day 0 and serum samples were collected on day 1-3 pi. Average viral copy numbers on day 1-2 were measured using mixed serum of each group. Viral copy number on day 3 was measured individually and the graphs show the average results with standard deviations. A P value less than 0.05 was considered significant (*P<0.05). (C) Administration of celgosivir at 50 mg/kg BID was started on day 3 and serum samples were collected on day 3-6 pi. Viral copy number on day 3-6 was measured individually and shown in the graphs as the average results with standard deviations. The VLR from day 3 to day 6 was also shown as the mean value and standard deviations. The number of mice per group is 6.
Figure 6:
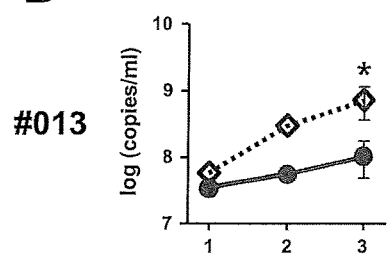
Figure 6:
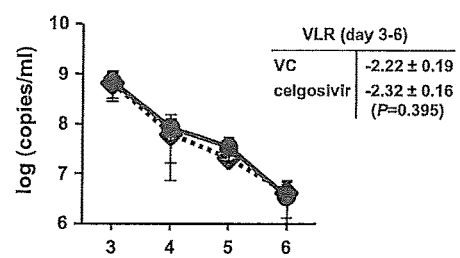
Figure 6:
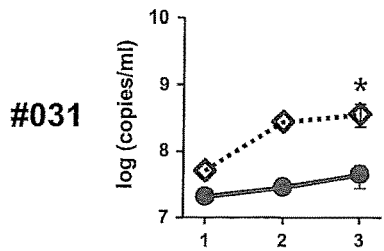
Figure 6:
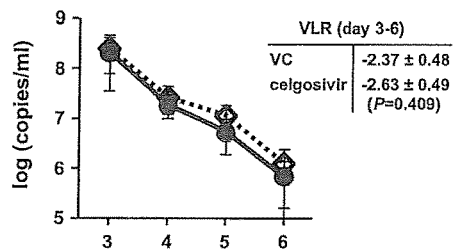
Figure 6:
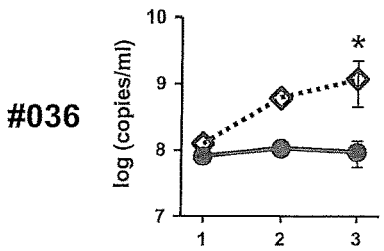
Figure 6:
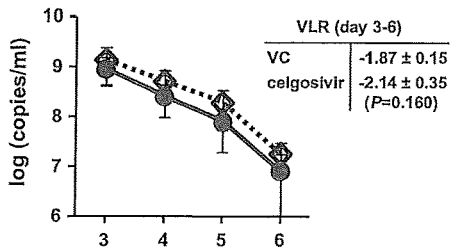
Figure 8:
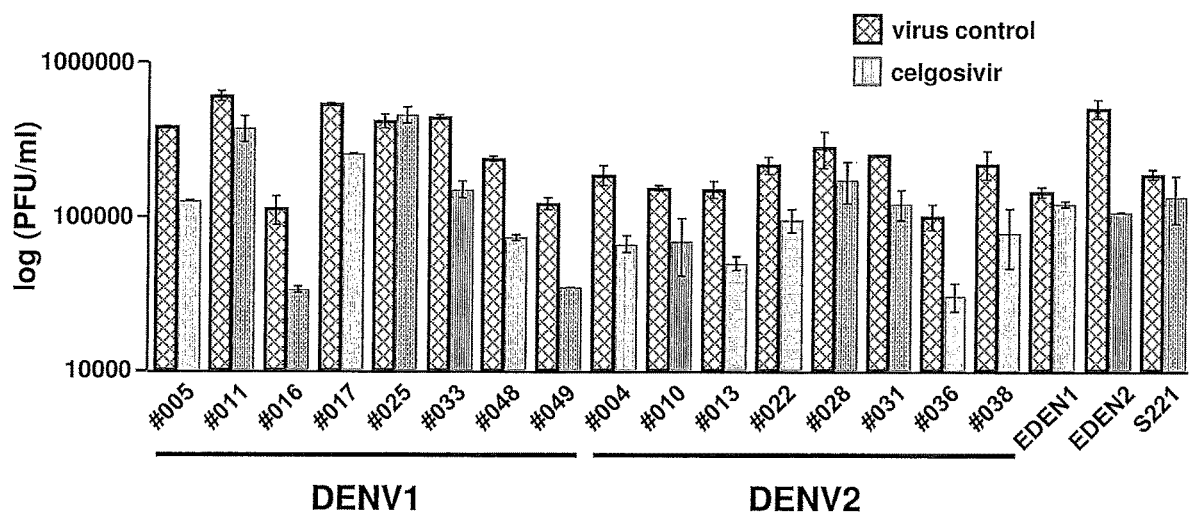
FIG. 8 shows the efficacy of celgosivir against clinical DENV strains obtained from CELADEN trial patients in HuH-7 cells. Total 16 clinical DENV virus were recovered from serum of CELADEN trial patients with 8 of either DENV1 or DENV2 infection. The strains as well as EDEN1, EDEN2 and S221 were used for infection in HuH-7 cells in the absence or presence of celgosivir at the concentration of 3 µM. The MOI was varied among strains to obtain similar levels of virus titer (within 10-fold difference). The MOI was 0.01 (EDEN1), 0.1 (#005, #048, #004, #033, #010, #013, #022, #036), 0.2 (#016, #017, #011, EDEN2, S221), 0.5 (#049, #038), 1 (#028, #031) and 2 (#025). After 48 hours post-infection, virus titer in the supernatants was determined by standard plaque assay using BHK-21 cells. Error bars indicate standard deviations from duplicate experiments.

Example 4: Celgosivir is Highly Effective Against Virus Amplified from CELADEN Patients To find out if the lack of efficacy of celgosivir in humans might reflect diminished drug sensitivity of the infecting viral strains, we next tested virus samples amplified in C6/36 cells from pre-treated serum of 16 CELADEN patients (8 each of DENV1 and DENV2) and subjected them to celgosivir administration at a single concentration of 3 mM in HuH-7 cells. Since infection levels in HuH-7 cells are different among the strains, the MOI of each strain was varied to obtain similar levels of virus titer in the supernatant (FIG. 8). Among 16 virus, only one strain (DENV1 #025) was found to be less sensitive to celgosivir than EDEN1 (FIG. 6A), and all others showed better sensitivity than EDEN1 or S221, suggesting that most of DENV strains in CELADEN patients are highly sensitive to celgosivir in vitro irrespective of their serotype or genotype. We selected three DENV2 strains, #013, #031 and #036, which showed 67%, 52% and 70% reduction in virus titer in the supernatant of HuH-7 cells, respectively (FIG. 3A), and tested their sensitivity to celgosivir in a non-lethal mouse model. When the administration at 50 mg/kg BID was started at the time of infection, viremia on day 3 pi showed significant reduction, with 6.8-fold (P=0.00127), 7.8-fold (F=0.0002) and 12.5-fold (F=0.0041) for #013, #031 and #036 infection, respectively (FIG. 6B). On the other hand, when treatment was started during peak viremia, VLR from day 3 to day 6 were 2.22 (VC) and 2.32 (celgosivir) (P=0.395) for #013, 2.37 (VC) and 2.63 (celgosivir)(P=0.409) for #031, and 1.87 (VC) and 2.14 (celgosivir) (P=0.160) for #036 infection (FIG. 6C). Thus, although clear inhibitory effect of celgosivir was demonstrated against CELADEN strains in mice, the effect became inconspicuous when treatment was started during peak viremia.

REFERENCES

1. WHO (2009). "Dengue and dengue hemorrhagic fever fact sheet 117." World Health Organization.
2. Fink J, Gu F and Vasudevan S G (2006). "Role of T cells, cytokines and antibody in dengue fever and dengue haemorrhagic fever." Rev Med Virol 16(4): 263-75.
3. Halstead S B (2007). "Dengue." Lancet 370(9599): 1644-52.
4. Remme J H, Blas E, Chitsulo L et al. (2002). "Strategic emphases for tropical diseases research: a TDR perspective." Trends Parasitol 18(10): 421-6.
5. Courageot M P, Frenkiel M P, Dos Santos C D et al. (2000). "Alpha-glucosidase inhibitors reduce dengue virus production by affecting the initial steps of virion morphogenesis in the endoplasmic reticulum." Journal of Virology 74(1): 564-72.
6. Rathore A P S, Paradkar P N, Watanabe S et al. (2011). "Celgosivir treatment misfolds dengue virus NS1 protein, induces cellular pro-survival genes and protects against lethal challenge mouse model." ANTIVIRAL RESEARCH 92(3): 453-60.
7. Ng C Y, Gu F, Phong W Y et al. (2007). "Construction and characterization of a stable subgenomic dengue virus type 2 replicon system for antiviral compound and siRNA testing." Antiviral Res 76(3): 222-31.
8. Schul W, Liu W, Xu H-Y et al. (2007). "A dengue fever viremia model in mice shows reduction in viral replication and suppression of the inflammatory response after treatment with antiviral drugs." J INFECT DIS 195(5): 665-74.
9. Zellweger R M, Prestwood T R and Shresta S (2010). "Enhanced infection of liver sinusoidal endothelial cells in a mouse model of antibody-induced severe dengue disease." Cell Host Microbe 7(2): 128-39.
10. Durantel D (2009). "Celgosivir, an alpha-glucosidase I inhibitor for the potential treatment of HCV infection." Curr Opin Investig Drugs 10(8): 860-70.
11. Erfle D, Rubinchik E, Pasetka H et al. (2005). "Pharmacokinetics of celgosivir (MX-3253), a novel a-glucosidase I inhibitor in loperamide-treated and diarrhea-induced rats." Antiviral Research 65: 1-1.
12. Sorbera L A, Castaner J and Garcia-Capdevila L (2005). "Celgosivir." Drugs of the Future 30(6): 545-552.
13. Roth H, McPherson M, Hamedani P et al. (1996). "Phase I tolerance and pharmacokinetics of a new castanospermine derivative, MDL 28,574A." Int Conf AIDS Abstracts: 1-1.
14. Saul R, Ghidoni J J, Molyneux R J et al. (1985). "Castanospermine inhibits alpha-glucosidase activities and alters glycogen distribution in animals." Proc Natl Acad Sci USA 82(1): 93-7.
15. Stoltz M and Arumugham T (1996). "Single and multiple dose proportionality study of MDL 28,574. Study No. NDPR0005." Hoeschst Marion Roussel (Report No. K-96-0262-D): 579p.
16. Beal S L, Sheiner L B, Boeckmann A J, Bauer R J. "NONMEM Users Guides." ICON Development Solutions, Ellicott City, M D, USA. 1989-2011.
17. R Core Team. R: "A Language and Environment for Statistical Computing." R Foundation for Statistical Computing, Vienna, Austria, 2013.
18. L. Sorbera, J. Castaner and L. Garcia-Capdevila, "Celgosivir," *Drugs of the Future,* vol. 30, no. 6, pp. 545-552, 2005.
19. C. Sung, S. Vasudevan, J. Low and E. Ooi, "Celgosivir Investigator's Brochure," Duke-NUS Graduate Medical School, Singapore, 2012.
20. Duke-NUS Graduate Medical School Program for Emerging Infectious Diseases, "Clinical Protocol EID-DF-01 Celgosivir Proof of Concept Trial for Treatment of Acute Dengue Fever (CELADEN)," 2012.
21. Bhatt, S., Gething, P. W., Brady, O. J., Messina, J. P., Farlow, A. W., Moyes, C. L., Drake, J. M., Brownstein, J. S., Hoen, A. G., Sankoh, O., Myers, M. F., George, D. B., Jaenisch, T., Wint, G. R., Simmons, C. P., Scott, T. W., Farrar, J. J., Hay, S. I., 2013. The global distribution and burden of dengue. Nature 496, 504-507.
22. Carocci, M., Hinshaw, S. M., Rodgers, M. A., Villareal, V. A., Burri, D. J., Pilankatta, R., Maharaj, N. P., Gack, M. U., Stavale, E. J., Warfield, K. L., Yang, P. L., 2015. The bioactive lipid 4-hydroxyphenyl retinamide inhibits *flavivirus* replication. Antimicrobial agents and chemotherapy 59, 85-95.
23. Chang, J., Schul, W., Butters, T. D., Yip, A., Liu, B., Goh, A., Lakshminarayana, S. B., Alonzi, D., Reinkensmeier, G., Pan, X., Qu, X., Weidner, J. M., Wang, L., Yu, W., Borune, N., Kinch, M. A., Rayahin, J. E., Moriarty, R., Xu, X., Shi, P. Y., Guo, J. T., Block, T. M., 2011. Combination of alpha-glucosidase inhibitor and ribavirin for the treatment of dengue virus infection in vitro and in vivo. Antiviral research 89, 26-34.
24. Chen, Y. L., Abdul Ghafar, N., Karuna, R., Fu, Y., Lim, S. P., Schul, W., Gu, F., Herve, M., Yokohama, F., Wang, G., Cerny, D., Fink, K., Blasco, F., Shi, P. Y., 2014.

Activation of peripheral blood mononuclear cells by dengue virus infection depotentiates balapiravir. Journal of virology 88, 1740-1747. Desmyter, J., Melnick, J. L., Rawls, W. E., 1968. Defectiveness of interferon production and of rubella virus interference in a line of African green monkey kidney cells (Vero). Journal of virology 2, 955-961.

25. Duyen, H. T., Ngoc, T. V., Ha do, T., Hang, V. T., Kieu, N. T., Young, P. R., Farrar, J. J., Simmons, C. P., Wolbers, M., Wills, B. A., 2011. Kinetics of plasma viremia and soluble nonstructural protein 1 concentrations in dengue: differential effects according to serotype and immune status. The Journal of infectious diseases 203, 1292-1300.

26. Fraser, J. E., Watanabe, S., Wang, C., Chan, W. K., Maher, B., Lopez-Denman, A., Hick, C., Wagstaff, K. M., Mackenzie, J. M., Sexton, P. M., Vasudevan, S. G., Jans, D. A., 2014. A nuclear transport inhibitor that modulates the unfolded protein response and provides in vivo protection against lethal dengue virus infection. The Journal of infectious diseases 210, 1780-1791.

27. Gubler, D. J., 2006. Dengue/dengue haemorrhagic fever: history and current status. Novartis Foundation symposium 277, 3-16; discussion 16-22, 71-13, 251-253.

28. Halstead, S. B., 2007. Dengue. Lancet 370, 1644-1652.

29. Keller, T. H., Chen, Y. L., Knox, J. E., Lim, S. P., Ma, N. L., Patel, S. J., Sampath, Wang, Q. Y., Yin, Z., Vasudevan, S. G., 2006. Finding new medicines for flaviviral targets. Novartis Foundation symposium 277, 102-114; discussion 114-109, 251-103.

30. Low, J. G., Ooi, E. E., Tolfvenstam, T., Leo, Y. S., Hibberd, M. L., Ng, L. C., Lai, Y. L., Yap, G. S., Li, C. S., Vasudevan, S. G., Ong, A., 2006. Early Dengue infection and outcome study (EDEN)—study design and preliminary findings. Annals of the Academy of Medicine, Singapore 35, 783-789.

31. Low, J. G., Sung, C., Wijaya, L., Wei, Y., Rathore, A. R, Watanabe, S., Tan, H., Toh, L., Chua, L. T., Hou, Y., Chow, A., Howe, S., Chan, W. K., Tan, K. H., Chung, J. S., Cherng, B. P., Lye, D. C., Tambayah, P. A., Ng, L. C., Connolly, J., Hibberd, M. L., Leo, Y. S., Cheung, Y. B., Ooi, E. E., Vasudevan, S. G., 2014. Efficacy and safety of celgosivir in patients with dengue fever (CELADEN): a phase 1b, randomised, double-blind, placebo-controlled, proof-of-concept trial. The Lancet. Infectious diseases 14, 706-715.

32. MacDonald, M. R., Machlin, E. S., Albin, O. R., Levy, D. E., 2007. The zinc finger antiviral protein acts synergistically with an interferon-induced factor for maximal activity against alphaviruses. Journal of virology 81, 13509-13518.

33. Mehta, A., Zitzmann, N., Rudd, P. M., Block, T. M., Dwek, R. A., 1998. Alpha-glucosidase inhibitors as potential broad based anti-viral agents. FEBS letters 430, 17-22.

34. Navarro-Sanchez, E., Altmeyer, R., Amara, A., Schwartz, O., Fieschi, F., Virelizier, J. L., Arenzana-Seisdedos, F., Despres, P., 2003. Dendritic-cell-specific ICAM3-grabbing non-integrin is essential for the productive infection of human dendritic cells by mosquito-cell-derived dengue viruses. EMBO reports 4, 723-728.

35. Nguyen, N. M., Tran, C. N., Phung, L. K., Duong, K. T., Huynh Hle, A., Farrar, J., Nguyen, Q. T., Tran, H. T., Nguyen, C. V, Merson, L., Hoang, L. T., Hibberd, M. L., Aw, P. P., Wilm, A., Nagarajan, N., Nguyen, D. T., Pham, M. P., Nguyen, T. T., Javanbakht, H., Klumpp, K., Hammond, J., Petric, R., Wolbers, M., Nguyen, C. T., Simmons, C. P., 2013. A randomized, double-blind placebo controlled trial of balapiravir, a polymerase inhibitor, in adult dengue patients. The Journal of infectious diseases 207, 1442-1450.

36. Perry, S. T., Buck, M. D., Plummer, E. M., Penmasta, R. A., Batra, H., Stavale, E. J., Warfield, K. L., Dwek, R. A., Butters, T. D., Alonzi, D. S., Lada, S. M., King, K., Klose, B., Ramstedt, U., Shresta, S., 2013. An iminosugar with potent inhibition of dengue virus infection in vivo. Antiviral research 98, 35-43.

37. Rathore, A. P., Paradkar, P. N., Watanabe, S., Tan, K. H., Sung, C., Connolly J. E., Low, J., Ooi, E. E., Vasudevan, S. G., 2011. Celgosivir treatment misfolds dengue virus NS1 protein, induces cellular pro-survival genes and protects against lethal challenge mouse model. Antiviral research 92, 453-460.

38. Reagan-Shaw, S., Nihal, M., Ahmad, N., 2008. Dose translation from animal to human studies revisited. FASEB journál: official publication of the Federation of American Societies for Experimental Biology 22, 659-661.

39. Schul, W., Liu, W., Xu, H. Y., Flamand, M., Vasudevan, S. G., 2007. A dengue fever viremia model in mice shows reduction in viral replication and suppression of the inflammatory response after treatment with antiviral drugs. The Journal of infectious diseases 195, 665-674.

40. Simmons, C. P., Farrar, J. J., Nguyen v, V., Wills, B., 2012. Dengue. The New England journal of medicine 366, 1423-1432.

41. Tricou, V., Minh, N. N., Farrar, J., Tran, H. T., Simmons, C. P., 2011. Kinetics of viremia and NS1 antigenemia are shaped by immune status and virus serotype in adults with dengue. PLoS neglected tropical diseases 5, e1309.

42. Tricou, V, Minh, N. N., Van, T. P., Lee, S. J., Farrar, J., Wills, B., Tran, H. T., Simmons, C. P., 2010. A randomized controlled trial of chloroquine for the treatment of dengue in Vietnamese adults. PLoS neglected tropical diseases 4, e785.

43. Watanabe, S., Chan, K. W., Wang, J., Rivino, L., Lok, S. M., Vasudevan, S. G., 2015. Dengue Virus Infection with Highly Neutralizing Levels of Cross-Reactive Antibodies Causes Acute Lethal Small Intestinal Pathology without a High Level of Viremia in Mice. Journal of virology 89, 5847-5861.

44. Watanabe, S., Rathore, A. P., Sung, C., Lu, F., Khoo, Y. M., Connolly, J., Low, J., Ooi, E. E., Lee, H. S., Vasudevan, S. G., 2012a. Dose- and schedule-dependent protective efficacy of celgosivir in a lethal mouse model for dengue virus infection informs dosing regimen for a proof of concept clinical trial. Antiviral research 96, 32-35.

45. Watanabe, S., Tan, K. H., Rathore, A. P., Rozen-Gagnon, K., Shuai, W., Ruedl, C., Vasudevan, S. G., 2012b. The magnitude of dengue virus NS1 protein secretion is strain dependent and does not correlate with severe pathologies in the mouse infection model. Journal of virology 86, 5508-5514.

46. Yauch, L. E., Zellweger, R. M., Kotturi, M. F., Qutubuddin, A., Sidney, J., Peters, B., Prestwood, T. R., Sette, A., Shresta, S., 2009. A protective role for dengue virus-specific CD8+ T cells. Journal of immunology 182, 4865-4873.

47. Yin, Z., Chen, Y. L., Schul, W., Wang, Q. Y., Gu, F., Duraiswamy, J., Kondreddi, R. R., Niyomrattanakit, P., Lakshminarayana, S. B., Goh, A., Xu, H. Y., Liu, W., Liu, B., Lim, J. Y., Ng, C. Y., Qing, M., Lim, C. C., Yip, A., Wang, G., Chan, W. L., Tan, H. P., Lin, K., Zhang, B., Zou, G., Bernard, K. A., Garrett, C., Beltz, K., Dong, M., Weaver, M., He, H., Pichota, A., Dartois, V., Keller, T. H., Shi, P. Y., 2009. An adenosine nucleoside inhibitor of dengue virus. Proceedings of the National Academy of Sciences of the United States of America 106, 20435-20439.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of preventing a disease resulting from a dengue virus (DENV) infection in a human subject, comprising:
    administering to the human subject at least one initial dose of about 40 to about 600 mg of a compound of Formula (II) or a pharmaceutically acceptable salt thereof, or a pharmaceutical composition comprising about 40 to about 600 mg of a compound of Formula (II) or a pharmaceutically acceptable salt thereof; and
    administering to the human subject a plurality of subsequent doses of about 25 to about 400 mg of a compound of Formula (II) or a pharmaceutically acceptable salt thereof, or a pharmaceutical composition comprising about 25 to about 400 mg of a compound of Formula (II) or a pharmaceutically acceptable salt thereof,
    wherein not more than 600 mg of a compound of Formula (II) is administered per day,
    wherein the human subject is asymptomatic at the time of administration of the at least one initial dose,
    wherein said subsequent doses are administered once, twice, three, or four times per day during potential exposure of at least one serotype of dengue virus, and wherein Formula (II) has the following structure,

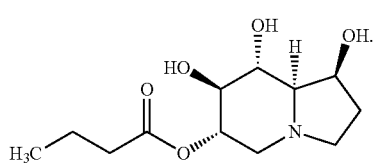

(II)

2. The method of claim 1, wherein the compound of Formula (II) is converted to castanospermine after administration to a human subject.

3. The method of claim 1, wherein a steady state Cmin serum or plasma concentration of between about 0.4 and about 2.0 microgram/mL of castanospermine in an adult or child human subject is attained after administrations of initial and subsequent doses.

4. The method of claim 1, wherein a steady state Cmin serum or plasma concentration of between about 1.0 and about 2.0 microgram/mL of castanospermine in an adult or child human subject is attained after administrations of the initial and subsequent doses.

5. The method of claim 1, wherein a steady state Cmin serum or plasma concentration of between about 1.0 and about 1.5 microgram/mL of castanospermine in an adult or child human subject is attained after administrations of the initial and subsequent doses.

6. The method of claim 1, wherein a steady state Cmin serum or plasma concentration of between about 1.5 and about 2.0 microgram/mL of castanospermine in an adult or child human subject is attained after administrations of the initial and subsequent doses.

7. The method of claim 1, wherein a steady state Cmin serum or plasma concentration of between about 1.25 and about 1.75 microgram/mL of castanospermine in an adult or child human subject is attained after administrations of the initial and subsequent doses.

8. The method of claim 1, wherein a steady state Cmin serum or plasma concentration of between about 0.4 and about 1 microgram/mL of castanospermine in an adult or child human subject is attained after administrations of the initial and subsequent doses.

9. The method of claim 1, wherein a steady state Cmin serum or plasma concentration of between about 0.75 and about 1.25 microgram/mL of castanospermine in an adult or child human subject is attained after administrations of the initial and subsequent doses.

10. The method of claim 1, wherein the dengue virus infection comprises at least one dengue virus selected from DENV1, DENV2, DENV3, and DENV4.

11. The method of claim 1, wherein the dengue virus infection is a secondary dengue infection.

12. The method of claim 1, wherein the compound, or the pharmaceutical composition, is administered orally or sublingually.

13. The method of claim 1, wherein the human subject is administered an initial dose of about 150 mg and is administered a subsequent dose of about 100 mg every 6 hours, 8 hours, or 12 hours for between about 5 days to about 30 days.

14. The method of claim 1, wherein the human subject is administered an initial dose of about 150 mg and is administered a subsequent dose of about 150 mg every 6 hours for between about 5 days to about 30 days.

15. The method of claim 1, wherein the human subject is administered an initial dose of about 150 mg and is administered a subsequent dose of about 150 mg every 8 hours for between about 5 days to about 30 days.

16. The method of claim 1, wherein the human subject is administered an initial dose of about 150 mg and is administered a subsequent dose of about 150 mg every 12 hours for between about 5 days to about 30 days.

17. The method of claim 1, wherein the human subject is administered an initial dose of about 150 mg and is administered a subsequent dose of about 200 mg every 6 hours, 8 hours, or 12 hours for between about 5 days to about 30 days.

18. The method of claim 1, wherein the human subject is administered an initial dose of about 200 mg and is administered a subsequent dose of about 100 mg every 6 hours, 8 hours, or 12 hours for between about 5 days to about 30 days.

19. The method of claim 1, wherein the human subject is administered an initial dose of about 200 mg and is administered a subsequent dose of about 150 every 6 hours, 8 hours, or 12 hours for between about 5 days to about 30 days.

20. The method of claim 1, wherein the human subject is administered an initial dose of about 200 mg and is administered a subsequent dose of about 200 mg every 6 hours, 8 hours, or 12 hours for between about 5 days to about 30 days.

21. The method of claim 1, wherein the human subject is administered a single or a divided dose of about 25 to about 300 mg of the compound or the pharmaceutical composition, for between about 5 days to about 30 days.

22. The method of claim 21, wherein the human subject is administered a divided dose of about 40 to about 300 mg per day of the compound, or the pharmaceutical composition, for about between about 5 days to about 30 days.

23. The method of claim 1, wherein the human subject is an adult.

24. The method of claim 1, wherein the human subject is a child.

* * * * *